United States Patent
Mao et al.

(10) Patent No.: US 11,352,474 B2
(45) Date of Patent: Jun. 7, 2022

(54) COMPOSITIONS IN THE FORM OF DISSOLVABLE SOLID STRUCTURES

(71) Applicant: The Procter & Gamble Company, Cincinnati, OH (US)

(72) Inventors: Min Mao, Deerfield Township, OH (US); Mark William Hamersky, Hamilton, OH (US); Robert Wayne Glenn, Jr., Liberty Township, OH (US); Todd Ryan Thompson, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 16/901,548

(22) Filed: Jun. 15, 2020

(65) Prior Publication Data
US 2020/0308360 A1    Oct. 1, 2020

Related U.S. Application Data

(60) Continuation of application No. 15/665,886, filed on Aug. 1, 2017, now Pat. No. 10,717,839, which is a division of application No. 14/690,593, filed on Apr. 20, 2015, now abandoned.

(60) Provisional application No. 61/982,736, filed on Apr. 22, 2014.

(51) Int. Cl.
| | |
|---|---|
| *C08J 9/00* | (2006.01) |
| *A61K 8/02* | (2006.01) |
| *B29C 39/00* | (2006.01) |
| *B29C 39/02* | (2006.01) |
| *B29C 67/20* | (2006.01) |
| *A61Q 5/02* | (2006.01) |
| *A61Q 5/12* | (2006.01) |
| *A61K 8/81* | (2006.01) |
| *B29L 7/00* | (2006.01) |

(52) U.S. Cl.
CPC ........... *C08J 9/0033* (2013.01); *A61K 8/0216* (2013.01); *A61K 8/8129* (2013.01); *A61Q 5/02* (2013.01); *A61Q 5/12* (2013.01); *B29C 39/003* (2013.01); *B29C 39/02* (2013.01); *B29C 67/20* (2013.01); *B29L 2007/002* (2013.01); *B29L 2007/008* (2013.01); *C08J 2329/06* (2013.01); *C08J 2331/04* (2013.01)

(58) Field of Classification Search
CPC .. C08J 9/0033; C08J 2331/04; C08J 2329/06; B29C 39/003; B29C 39/02; B29C 67/20; A61Q 5/02; A61Q 5/12; A61Q 11/00; A61Q 13/00; A61Q 15/00; A61Q 19/00; A61Q 19/10; A61K 8/8129; A61K 8/0216; A61K 8/0279; A61K 8/44; A61K 8/731; A61K 8/737; A61K 8/8135; A61K 8/86; A61K 2800/49; B29L 2007/002; B29L 2007/008; C11D 3/3761; D06M 13/207; D06M 13/463; D06M 15/333; D06M 15/53
See application file for complete search history.

(56) References Cited

U.S. PATENT DOCUMENTS

| | | |
|---|---|---|
| 2,356,168 A | 8/1941 | Mabley |
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer et al. |
| 2,613,185 A | 10/1952 | Marshall |
| 2,658,072 A | 11/1953 | Kosmin |
| 2,694,668 A | 11/1954 | Fricke |
| 2,809,971 A | 10/1957 | Bernstein |
| 3,152,046 A | 10/1964 | Kapral |
| 3,236,733 A | 2/1966 | Karsten |
| 3,321,425 A | 5/1967 | Blau et al. |
| 3,332,880 A | 7/1967 | Kessler |
| 3,426,440 A | 2/1969 | Shen |
| 3,428,478 A | 2/1969 | Donaldson et al. |
| 3,463,308 A | 8/1969 | Deneke |
| 3,489,688 A | 1/1970 | Pospischil |
| 3,653,383 A | 4/1972 | Wise |
| 3,695,989 A | 10/1972 | Albert |
| 3,753,196 A | 8/1973 | Kurtz |
| 3,761,418 A | 9/1973 | Parran, Jr. |
| 3,929,678 A | 12/1975 | Laughlin |
| 3,967,921 A | 7/1976 | Haberli |
| 4,020,156 A | 4/1977 | Murray |

(Continued)

FOREIGN PATENT DOCUMENTS

| | | |
|---|---|---|
| CA | 169627 S | 5/2018 |
| CN | 1138091 | 12/1996 |

(Continued)

OTHER PUBLICATIONS

Zhang et al. "Study on Morphology of Electrospun Poly(vinyl alcohol) Mats," European Polymer Journal 41:423-432, 2005.
Guerrini et al. "Thermal and Structural Characterization of Nanofibers of Poly(vinyl alcohol) Produced by Electrospinning," Journal of Applied Polymer Science 112(3):1680-1687, 2009.
AU Office Actions for U.S. Appl. No. 14/692,779, filed Apr. 22, 2015.
ISR dated Jul. 20, 2012, PCT/US2012/032253, 5 pages.
All Office Actions, U.S. Appl. No. 12/424,812.
All Office Actions, U.S. Appl. No. 12/633,257.

(Continued)

*Primary Examiner* — Kara B Boyle
(74) *Attorney, Agent, or Firm* — Alexandra S. Anoff

(57) ABSTRACT

Described are dissolvable, porous solid structures formed using certain vinyl acetate-vinyl alcohol copolymers. The copolymer and the porosity of the structure allow for liquid flow during use such that the structure readily dissolves to provide a desired consumer experience. Also described are processes for making open cell foam and fibrous dissolvable solid structures.

15 Claims, 1 Drawing Sheet

(56) References Cited

U.S. PATENT DOCUMENTS

| | | |
|---|---|---|
| 4,051,081 A | 9/1977 | Jabs et al. |
| 4,089,945 A | 5/1978 | Brinkman |
| 4,149,551 A | 4/1979 | Benjamin et al. |
| 4,185,125 A | 1/1980 | Kimura et al. |
| 4,196,190 A | 3/1980 | Gehman |
| 4,197,865 A | 4/1980 | Jacquet |
| 4,206,196 A | 6/1980 | Davis |
| 4,217,914 A | 8/1980 | Jacquet |
| 4,272,511 A | 6/1981 | Papantoniou |
| 4,323,683 A | 4/1982 | Bolich, Jr. |
| 4,345,080 A | 8/1982 | Bolich, Jr. |
| D266,829 S | 11/1982 | Yoshizawa et al. |
| 4,379,753 A | 4/1983 | Bolich, Jr. |
| 4,381,919 A | 5/1983 | Jacquet |
| 4,422,853 A | 12/1983 | Jacquet |
| 4,470,982 A | 9/1984 | Winkler |
| 4,507,280 A | 3/1985 | Pohl |
| 4,529,586 A | 7/1985 | De Marco |
| 4,536,361 A | 8/1985 | Torobin |
| 4,565,647 A | 1/1986 | Llenado |
| D286,450 S | 10/1986 | Tovey |
| 4,635,351 A | 1/1987 | Koch et al. |
| 4,663,158 A | 5/1987 | Wolfram |
| 4,710,374 A | 12/1987 | Grollier |
| 4,727,410 A | 2/1988 | Higgins, III |
| 4,822,613 A | 4/1989 | Rodero |
| 4,885,107 A | 12/1989 | Wetzel |
| 4,976,953 A | 12/1990 | Orr |
| 4,990,280 A | 2/1991 | Thorengaard et al. |
| 5,055,384 A | 10/1991 | Kuhnert |
| 5,061,481 A | 10/1991 | Suzuki |
| 5,062,889 A | 11/1991 | Hohl et al. |
| 5,062,994 A | 11/1991 | Imperatori |
| 5,094,853 A | 3/1992 | Hagerty |
| 5,098,636 A | 3/1992 | Balk |
| 5,100,657 A | 3/1992 | Ansher-Jackson |
| 5,100,658 A | 3/1992 | Bolich, Jr. |
| 5,102,129 A | 4/1992 | Roberts |
| 5,104,646 A | 4/1992 | Bolich, Jr. |
| 5,106,609 A | 4/1992 | Bolich, Jr. |
| 5,166,276 A | 11/1992 | Hayama |
| D334,420 S | 3/1993 | Copeland et al. |
| 5,220,033 A | 6/1993 | Kamei et al. |
| 5,261,426 A | 11/1993 | Kellett et al. |
| 5,280,079 A | 1/1994 | Allen |
| RE34,584 E | 4/1994 | Grote |
| D351,345 S | 10/1994 | Geho |
| 5,391,368 A | 2/1995 | Gerstein |
| D357,115 S | 4/1995 | Ashley et al. |
| 5,409,703 A | 4/1995 | McAnalley |
| D358,025 S | 5/1995 | Martin et al. |
| 5,415,810 A | 5/1995 | Lee |
| 5,429,628 A | 7/1995 | Trinh |
| 5,455,114 A | 10/1995 | Ohmory |
| 5,457,895 A | 10/1995 | Thompson et al. |
| 5,458,433 A | 10/1995 | Stastny |
| 5,476,597 A | 12/1995 | Sakata et al. |
| 5,501,238 A | 3/1996 | Von Borstel |
| 5,533,636 A | 7/1996 | Reiker |
| 5,580,481 A | 12/1996 | Sakata et al. |
| 5,582,786 A | 12/1996 | Brunskill |
| D378,180 S | 2/1997 | Hayes |
| 5,660,845 A | 8/1997 | Trinh |
| 5,672,576 A | 9/1997 | Behrens |
| 5,673,576 A | 9/1997 | Behrens |
| 5,674,478 A | 10/1997 | Dodd |
| 5,750,122 A | 5/1998 | Evans |
| 5,780,047 A | 5/1998 | Kamiya et al. |
| D398,847 S | 9/1998 | Wyslotsky |
| D399,260 S | 10/1998 | Thimote |
| D407,640 S | 4/1999 | Crapser et al. |
| D408,223 S | 4/1999 | Henry |
| 5,911,224 A | 6/1999 | Berger |
| 5,925,603 A | 7/1999 | D'Angelo |
| 5,955,419 A | 9/1999 | Barket, Jr. |
| D416,103 S | 11/1999 | Anaam |
| 5,976,454 A | 11/1999 | Sterzel et al. |
| D418,415 S | 1/2000 | Hayes |
| D418,750 S | 1/2000 | Blin |
| 6,010,719 A | 1/2000 | Remon |
| 6,029,808 A | 2/2000 | Peck et al. |
| 6,034,043 A | 3/2000 | Fujiwara |
| D427,902 S | 7/2000 | Hayes |
| 6,106,849 A | 8/2000 | Malkan et al. |
| 6,177,391 B1 | 1/2001 | Zafar |
| 6,200,949 B1 | 3/2001 | Reijmer |
| D441,869 S | 5/2001 | Bloor et al. |
| D442,353 S | 5/2001 | Macias |
| D442,739 S | 5/2001 | Friesenhahn |
| D443,389 S | 6/2001 | Friesenhahn |
| D448,802 S | 10/2001 | Lariviere, Jr. et al. |
| D449,881 S | 10/2001 | Mock, Sr. |
| D450,378 S | 11/2001 | Minakuchi et al. |
| 6,365,142 B1 | 4/2002 | Tamura |
| D462,900 S | 9/2002 | Yamada et al. |
| 6,458,754 B1 | 10/2002 | Velaquez |
| D465,303 S | 11/2002 | Friesenhahn |
| 6,503,521 B1 | 1/2003 | Atis et al. |
| 6,525,034 B2 | 2/2003 | Dalrymple et al. |
| D479,561 S | 9/2003 | Meyer |
| D484,749 S | 1/2004 | Garraway |
| D489,162 S | 5/2004 | Dings-Plooij |
| 6,790,814 B1 | 9/2004 | Marin |
| 6,800,295 B2 | 10/2004 | Fox |
| 6,802,295 B2 | 10/2004 | Fox |
| 6,808,375 B2 | 10/2004 | Klotzer |
| 6,825,161 B2 | 11/2004 | Shefer et al. |
| 6,831,046 B2 | 12/2004 | Carew et al. |
| 6,846,784 B2 | 1/2005 | Engel et al. |
| 6,878,368 B2 | 4/2005 | Ohta et al. |
| D509,935 S | 9/2005 | Burt |
| 6,943,200 B1 | 9/2005 | Corrand et al. |
| D515,915 S | 2/2006 | Karim |
| 7,015,181 B2 | 3/2006 | Lambino |
| 7,208,460 B2 | 4/2007 | Shefer et al. |
| D549,051 S | 8/2007 | Nordwall |
| 7,285,520 B2 | 10/2007 | Krzysik et al. |
| 7,387,787 B2 | 6/2008 | Fox |
| D576,753 S | 9/2008 | Kenji |
| D577,332 S | 9/2008 | Moore |
| D578,881 S | 10/2008 | Friedland |
| D588,332 S | 3/2009 | Phelan |
| 7,832,552 B2 | 11/2010 | Newman |
| 7,846,462 B2 | 12/2010 | Spadini et al. |
| 7,892,992 B2 | 2/2011 | Kamada |
| 7,901,696 B2 | 3/2011 | Eknoian |
| D640,921 S | 7/2011 | Caldwell |
| D644,541 S | 9/2011 | Schrader et al. |
| D651,096 S | 12/2011 | Nakagiri |
| D655,154 S | 3/2012 | Amos |
| 8,197,830 B2 | 6/2012 | Helfman et al. |
| 8,268,764 B2 | 9/2012 | Glenn, Jr. et al. |
| 8,273,333 B2 | 9/2012 | Glenn et al. |
| 8,288,332 B2 | 10/2012 | Fossum et al. |
| 8,309,505 B2 | 11/2012 | Fossum et al. |
| 8,349,341 B2 | 1/2013 | Glenn, Jr. et al. |
| 8,349,786 B2 | 1/2013 | Glenn et al. |
| 8,349,787 B2 | 1/2013 | Glenn et al. |
| 8,357,728 B2 | 1/2013 | Butler |
| D680,882 S | 4/2013 | Logue |
| 8,415,287 B2 | 4/2013 | Glenn, Jr. et al. |
| D682,622 S | 5/2013 | Keys |
| 8,461,090 B2 | 6/2013 | Glenn, Jr. et al. |
| 8,461,091 B2 | 6/2013 | Glenn, Jr. et al. |
| 8,466,099 B2 | 6/2013 | Glenn, Jr. et al. |
| D685,436 S | 7/2013 | Menting |
| 8,476,211 B2 | 7/2013 | Glenn, Jr. et al. |
| 8,546,640 B2 | 10/2013 | Popovsky et al. |
| D694,621 S | 12/2013 | McCarthy |
| 8,723,333 B2 | 5/2014 | Park et al. |
| 8,765,170 B2 | 7/2014 | Glenn, Jr. |
| D712,159 S | 9/2014 | Clerici et al. |
| D712,822 S | 9/2014 | Brusaw et al. |
| 9,062,186 B2 | 6/2015 | Longdon et al. |

(56) References Cited

U.S. PATENT DOCUMENTS

| | | |
|---|---|---|
| D739,227 S | 9/2015 | Mitchell et al. |
| D740,928 S | 10/2015 | Bruining et al. |
| 9,198,838 B2 | 12/2015 | Glenn, Jr. |
| D748,240 S | 1/2016 | Goode |
| D769,522 S | 10/2016 | Venet |
| D771,788 S | 11/2016 | Duckwitz |
| D774,086 S | 12/2016 | Montes et al. |
| D775,198 S | 12/2016 | Montes |
| 9,539,444 B2 | 1/2017 | Kinoshita et al. |
| D778,026 S | 2/2017 | Roetheli |
| D793,025 S | 8/2017 | Slusarczyk et al. |
| D797,551 S | 9/2017 | Chatterton |
| D798,143 S | 9/2017 | Chatterton |
| D808,583 S | 1/2018 | Zietek |
| D811,922 S | 3/2018 | Lefave |
| D811,935 S | 3/2018 | Hughes |
| D819,836 S | 6/2018 | Noël |
| D848,102 S | 5/2019 | Carlson et al. |
| D850,041 S | 5/2019 | Endle |
| D851,344 S | 6/2019 | Carlson et al. |
| D857,156 S | 8/2019 | Hani |
| D857,242 S | 8/2019 | Darrow et al. |
| D857,929 S | 8/2019 | Darrow et al. |
| D862,020 S | 10/2019 | Gorrell et al. |
| D863,600 S | 10/2019 | Chao |
| D864,507 S | 10/2019 | Stoughton et al. |
| D866,105 S | 11/2019 | Carlson |
| D866,891 S | 11/2019 | Carlson et al. |
| D866,892 S | 11/2019 | Hunt et al. |
| D866,893 S | 11/2019 | Hunt et al. |
| D867,717 S | 11/2019 | Chavez |
| D868,159 S | 11/2019 | Swisher et al. |
| D868,953 S | 12/2019 | Mckendree |
| 10,569,286 B2 | 2/2020 | Anderson et al. |
| D878,694 S | 3/2020 | Carlson et al. |
| 10,694,917 B2 | 6/2020 | Dreher et al. |
| D901,115 S | 11/2020 | Carlson et al. |
| D903,152 S | 11/2020 | Chao |
| D906,802 S | 1/2021 | Chi |
| D910,434 S | 2/2021 | Tan et al. |
| D910,457 S | 2/2021 | Lee |
| D921,166 S | 6/2021 | Meyers |
| D933,095 S | 10/2021 | Heiner et al. |
| 2002/0077264 A1 | 6/2002 | Roberts et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0177621 A1 | 11/2002 | Hanada |
| 2002/0187181 A1 | 12/2002 | Godbey et al. |
| 2003/0018242 A1 | 1/2003 | Hursh et al. |
| 2003/0032573 A1 | 2/2003 | Tanner et al. |
| 2003/0045441 A1 | 3/2003 | Hsu et al. |
| 2003/0069154 A1 | 4/2003 | Hsu et al. |
| 2003/0080150 A1 | 5/2003 | Cowan et al. |
| 2003/0099691 A1 | 5/2003 | Lydzinski |
| 2003/0099692 A1 | 5/2003 | Lydzinski et al. |
| 2003/0141662 A1 | 7/2003 | Kost et al. |
| 2003/0180242 A1 | 9/2003 | Eccard et al. |
| 2003/0186826 A1 | 10/2003 | Eccard et al. |
| 2003/0194416 A1 | 10/2003 | Shefer |
| 2003/0199412 A1 | 10/2003 | Gupta |
| 2003/0209166 A1 | 11/2003 | Vanmaele et al. |
| 2003/0215522 A1 | 11/2003 | Johnson |
| 2003/0232183 A1 | 12/2003 | Dufton |
| 2004/0029762 A1 | 2/2004 | Hensley |
| 2004/0032859 A1 | 2/2004 | Mino |
| 2004/0048759 A1 | 3/2004 | Ribble et al. |
| 2004/0048771 A1 | 3/2004 | Mcdermott |
| 2004/0053808 A1 | 3/2004 | Raehse et al. |
| 2004/0059055 A1 | 3/2004 | Inada |
| 2004/0071742 A1 | 4/2004 | Popplewell |
| 2004/0071755 A1 | 4/2004 | Fox |
| 2004/0108615 A1 | 6/2004 | Foley |
| 2004/0110656 A1 | 6/2004 | Casey |
| 2004/0126585 A1 | 7/2004 | Kerins et al. |
| 2004/0175404 A1 | 9/2004 | Shefer |
| 2004/0180597 A1 | 9/2004 | Kamada |
| 2004/0202632 A1 | 10/2004 | Gott |
| 2004/0206270 A1 | 10/2004 | Vanmaele |
| 2004/0242097 A1 | 12/2004 | Hasenoehrl et al. |
| 2004/0242772 A1 | 12/2004 | Huth et al. |
| 2005/0069575 A1 | 3/2005 | Fox |
| 2005/0136780 A1 | 6/2005 | Clark et al. |
| 2005/0137272 A1 | 6/2005 | Gaserod et al. |
| 2005/0159730 A1 | 7/2005 | Kathrani et al. |
| 2005/0202992 A1 | 9/2005 | Grandio Portabales |
| 2005/0220745 A1 | 10/2005 | Lu |
| 2005/0232954 A1 | 10/2005 | Yoshinari |
| 2005/0272836 A1 | 12/2005 | Yaginuma et al. |
| 2005/0287106 A1 | 12/2005 | Legandre |
| 2006/0013869 A1 | 1/2006 | Ignatious et al. |
| 2006/0052263 A1 | 3/2006 | Roreger |
| 2006/0064510 A1 | 3/2006 | Low et al. |
| 2006/0078528 A1 | 4/2006 | Yang |
| 2006/0078529 A1 | 4/2006 | Uchida |
| 2006/0128592 A1 | 6/2006 | Ross |
| 2006/0159730 A1 | 7/2006 | Simon |
| 2006/0002880 A1 | 10/2006 | Peffly |
| 2006/0228319 A1 | 10/2006 | Vona, Jr. et al. |
| 2006/0274263 A1 | 12/2006 | Yacktman et al. |
| 2007/0028939 A1 | 2/2007 | Mareri et al. |
| 2007/0099813 A1 | 5/2007 | Luizzi |
| 2007/0110792 A9 | 5/2007 | Simon |
| 2007/0135528 A1 | 6/2007 | Butler et al. |
| 2007/0149435 A1 | 6/2007 | Koenig |
| 2007/0225388 A1 | 9/2007 | Cooper et al. |
| 2008/0019935 A1 | 1/2008 | Khan |
| 2008/0035174 A1 | 2/2008 | Aubrun-Sonneville et al. |
| 2008/0083420 A1 | 4/2008 | Glenn et al. |
| 2008/0090939 A1 | 4/2008 | Netravali et al. |
| 2008/0131695 A1 | 6/2008 | Aouad |
| 2008/0138492 A1 | 6/2008 | Cingotti |
| 2008/0152894 A1 | 6/2008 | Beihoffer |
| 2008/0153730 A1 | 6/2008 | Tsaur |
| 2008/0215023 A1 | 9/2008 | Scavone |
| 2008/0276178 A1 | 11/2008 | Fadell |
| 2008/0292669 A1 | 11/2008 | Deng et al. |
| 2008/0293839 A1 | 11/2008 | Stobby |
| 2009/0197787 A1 | 8/2009 | Venet et al. |
| 2009/0232873 A1 | 9/2009 | Glenn et al. |
| 2009/0263342 A1* | 10/2009 | Glenn, Jr ............. A61K 8/8129 424/70.11 |
| 2010/0018641 A1 | 1/2010 | Branham |
| 2010/0150976 A1 | 6/2010 | Schnitzler |
| 2010/0167971 A1 | 7/2010 | Glenn, Jr. |
| 2010/0173817 A1 | 7/2010 | Glenn, Jr. |
| 2010/0286011 A1 | 11/2010 | Glenn, Jr. et al. |
| 2010/0291165 A1 | 11/2010 | Glenn, Jr. |
| 2011/0023240 A1 | 2/2011 | Fossum |
| 2011/0027328 A1 | 2/2011 | Baig et al. |
| 2011/0028374 A1 | 2/2011 | Fossum |
| 2011/0033509 A1 | 2/2011 | Simon |
| 2011/0165110 A1 | 7/2011 | Kinoshita et al. |
| 2011/0182956 A1 | 7/2011 | Glenn, Jr. |
| 2011/0189247 A1 | 8/2011 | Glenn, Jr. |
| 2011/0195098 A1 | 8/2011 | Glenn, Jr. |
| 2011/0250256 A1 | 10/2011 | Hyun-Oh et al. |
| 2011/0287687 A1 | 11/2011 | Kramer et al. |
| 2012/0021026 A1* | 1/2012 | Glenn, Jr ............. A61K 8/0233 424/401 |
| 2012/0052036 A1 | 3/2012 | Glenn, Jr. |
| 2012/0052037 A1 | 3/2012 | Sivik et al. |
| 2012/0107534 A1 | 5/2012 | Wnuk et al. |
| 2012/0237576 A1 | 9/2012 | Gordon |
| 2012/0270029 A1 | 10/2012 | Granberg et al. |
| 2012/0294823 A1 | 11/2012 | Aramwit |
| 2012/0321580 A1 | 12/2012 | Glenn, Jr. et al. |
| 2013/0236520 A1 | 9/2013 | Popovsky et al. |
| 2013/0303419 A1 | 11/2013 | Glenn, Jr. et al. |
| 2014/0271744 A1 | 9/2014 | Glenn, Jr. et al. |
| 2014/0329428 A1 | 11/2014 | Glenn, Jr. |
| 2015/0102307 A1 | 4/2015 | Tajima et al. |
| 2015/0297494 A1 | 10/2015 | Mao |
| 2015/0313803 A1 | 11/2015 | Lynch |

(56) References Cited

U.S. PATENT DOCUMENTS

| | | |
|---|---|---|
| 2015/0313804 A1 | 11/2015 | Lynch |
| 2015/0313805 A1 | 11/2015 | Lynch |
| 2015/0313806 A1 | 11/2015 | Lynch |
| 2015/0313807 A1 | 11/2015 | Lynch |
| 2015/0313808 A1 | 11/2015 | Lynch |
| 2015/0313809 A1 | 11/2015 | Lynch |
| 2015/0315350 A1 | 11/2015 | Mao et al. |
| 2016/0101026 A1 | 4/2016 | Pratt |
| 2016/0101204 A1 | 4/2016 | Lynch |
| 2016/0143827 A1 | 5/2016 | Castan Barberan |
| 2016/0250109 A1 | 9/2016 | Dreher |
| 2016/0367104 A1 | 12/2016 | Dreher et al. |
| 2017/0121641 A1 | 5/2017 | Smith |
| 2017/0335080 A1 | 11/2017 | Mao et al. |
| 2018/0140469 A1 | 5/2018 | Kane et al. |
| 2018/0333339 A1 | 11/2018 | Hamersky |
| 2019/0015875 A1 | 1/2019 | Gardner, Jr. |
| 2019/0282457 A1 | 9/2019 | Pratt |
| 2019/0282461 A1 | 9/2019 | Glassmeyer |
| 2020/0093710 A1 | 3/2020 | Hamersky |
| 2020/0214946 A1 | 7/2020 | Chan et al. |
| 2020/0405587 A1 | 12/2020 | Song |
| 2021/0000733 A1 | 1/2021 | Hilvert |
| 2021/0094744 A1 | 4/2021 | Benson et al. |
| 2021/0107263 A1 | 4/2021 | Bartolucci et al. |
| 2021/0147763 A1 | 5/2021 | Tan et al. |
| 2021/0401677 A1 | 12/2021 | Song |

FOREIGN PATENT DOCUMENTS

| | | |
|---|---|---|
| CN | 1219388 A | 6/1999 |
| CN | 1268558 A | 10/2000 |
| CN | 1357613 | 7/2002 |
| CN | 1473194 A | 2/2004 |
| CN | 1530431 | 9/2004 |
| CN | 1583991 A | 2/2005 |
| CN | 3648760 | 5/2007 |
| CN | 102006852 A | 4/2011 |
| CN | 301666535 | 9/2011 |
| CN | 102647973 A | 8/2012 |
| CN | 103282015 A | 9/2013 |
| CN | 103735428 A | 4/2014 |
| CN | 104040061 A | 9/2014 |
| CN | 304115833 | 4/2017 |
| CN | 106726634 A | 5/2017 |
| CN | 106728634 A | 5/2017 |
| CN | 304537587 | 3/2018 |
| DE | 19607851 A1 | 9/1997 |
| DE | 10331767 A1 | 2/2005 |
| DE | DM100932 | 4/2018 |
| DE | DM100938 | 4/2018 |
| DE | DM101063 | 5/2018 |
| DE | DM101100 | 5/2018 |
| DE | DM101101 | 5/2018 |
| EP | 609808 A1 | 8/1994 |
| EP | 0858828 A1 | 8/1998 |
| EP | 1160311 B1 | 12/2001 |
| EP | 1217987 B1 | 12/2004 |
| EP | 1958532 A2 | 8/2008 |
| EP | 2085434 A1 | 8/2009 |
| EP | 1317916 B1 | 10/2010 |
| FR | 2871685 A1 | 12/2005 |
| FR | 2886845 A1 | 12/2006 |
| GB | 2235204 A | 2/1991 |
| GB | 2355008 A | 4/2001 |
| JP | 58021608 | 2/1983 |
| JP | 58216109 | 12/1983 |
| JP | 62-072609 | 4/1987 |
| JP | 62-072610 | 4/1987 |
| JP | 62-081432 | 4/1987 |
| JP | H01172319 A | 7/1989 |
| JP | 01313418 | 12/1989 |
| JP | H0275650 A | 3/1990 |
| JP | 5344873 A | 12/1993 |
| JP | 6017083 A | 1/1994 |
| JP | 07-53349 | 2/1995 |
| JP | 7089852 A | 4/1995 |
| JP | 1998325133 A | 12/1996 |
| JP | H09216909 A | 8/1997 |
| JP | 10251371 A1 | 9/1998 |
| JP | 2000053998 A | 2/2000 |
| JP | 200373700 A | 3/2003 |
| JP | 200382397 | 3/2003 |
| JP | 2004256799 A | 9/2004 |
| JP | 2004345983 A | 12/2004 |
| JP | 2005171063 A | 6/2005 |
| JP | 2007197540 A | 8/2007 |
| JP | 2007091954 A | 12/2007 |
| KR | 2002-0003442 | 1/2002 |
| KR | 20020003442 A | 1/2002 |
| WO | 83/01943 A1 | 11/1992 |
| WO | 1995/014495 A1 | 6/1995 |
| WO | 2001/19948 A1 | 3/2001 |
| WO | 2001/024770 A1 | 4/2001 |
| WO | 2001/25322 A1 | 4/2001 |
| WO | 2001/25393 A1 | 4/2001 |
| WO | 01/54667 A1 | 8/2001 |
| WO | 2004/032859 A | 4/2004 |
| WO | 2004/041991 A1 | 5/2004 |
| WO | 2005/003423 A1 | 1/2005 |
| WO | 2005070374 A1 | 8/2005 |
| WO | 2005075547 A1 | 8/2005 |
| WO | 2007/033598 A1 | 3/2007 |
| WO | 2007/093558 A1 | 8/2007 |
| WO | 2009/019571 A1 | 2/2009 |
| WO | 2009095891 A1 | 8/2009 |
| WO | 2010077627 A2 | 7/2010 |
| WO | 2010085569 A1 | 7/2010 |
| WO | 2012120199 A1 | 9/2012 |
| WO | 2019001940 A1 | 1/2019 |

OTHER PUBLICATIONS

All Office Actions, U.S. Appl. No. 12/633,301.
All Office Actions, U.S. Appl. No. 12/633,550.
All Office Actions, U.S. Patent Appl. No. 12/633,335.
All Office Actions, U.S. Appl. No. 12/633,415.
All Office Actions, U.S. Appl. No. 12/633,572.
All Office Actions, U.S. Appl. No. 12/361,634.
All Office Actions, U.S. Appl. No. 12/962,846.
All Office Actions, U.S. Appl. No. 12/962,873.
All Office Actions, U.S. Appl. No. 12/962,888.
All Office Actions, U.S. Appl. No. 12/962,905.
All Office Actions, U.S. Appl. No. 13/173,639.
All Office Actions, U.S. Appl. No. 13/440,475.
All Office Actions, U.S. Appl. No. 13/597,539.
All Office Actions, U.S. Patent Appl. No. 13/561,298.
Pure Soap Leafz: (Soap UNLTD, Netherlands, http://www.upandunder.co.uk/eshop/catalogue/testbs.asp?Manufacturer_ID=252&Activity_ID=33& Description_ID=157).
Dissolving Soap Strips (Ranir LLC, Michigan, www.ranir.com).
Japanese Paper Soap (http://www.wishingfish.com/papersoap.html).
Travelers Passport Paper Soap Sheets (http://www.weddingfavorsnow.com/index.asp?PageAction=VIEWPROD&ProdID=510).
ISR dated May 6, 2011, PCT/US2009/067130, 5 pages.
ISR dated May 4, 2011, PCT/US2009/067088, 5 pages.
ISR dated Jul. 19, 2011, PCT/US2009/067088, 7 pages.
ISR dated May 9, 2011, PCT/US2009/067132, 5 pages.
ISR dated Jul. 20, 2011, PCT/US2009/067131, 5 pages.
ISR dated Apr. 29, 2011, PCT/US2009/067089, 5 pages.
ISR dated Jul. 15, 2009, PCT/IB2009/050388, 8 pages.
ISR dated Aug. 17, 2009, PCT/US2009/040739, 6 pages.
ISR dated Nov. 4, 2009, PCT/US2009/040739, 10 pages.
ISR dated Dec. 15, 2011, PCT/US2009/067087, 5 pages.
ISR dated Jul. 19, 2011, PCT/US2009/067133, 4 pages.
ISR dated Jul. 19, 2011, PCT/US2009/067130, 7 pages.
ISR dated Apr. 27, 2011, PCT/US2010/059365, 5 pages.
ISR dated Apr. 27, 2011, PCT/US2010/059455, 5 pages.
ISR dated Apr. 27, 2011, PCT/US2010/059359, 5 pages.
ISR dated Jun. 7, 2013, PCT/US2010/059441, 9 pages.

(56) References Cited

OTHER PUBLICATIONS

ISR dated Feb. 20, 2013, PCT/US2011/042640, 12 pages.
C. D. Vaughan. Solubility, Effects in Product, Package, Penetration and Preservation, Cosmetics and Toiletries, vol. 103, Oct. 1988.
Encyclopedia of Polymer Science and Engineering, vol. 15, 2d ed., p. 204 308, John Wiley & Sons, Inc. (1989).
Anonymous: "P8136 Poly(vinyl alcohol)" Internet article, [Online] XP002538935 Retrieved from the Internet: URL:http://www.sigmaaldrich.com/catalog/ProductDetail.do?D7-0&N25-SEARCH_CONCAT_PNO%7CBRAND_KEY&N4=P8136%7CSIAL&N25=0&QS=0N&F=SPEC> [retrieved on Jul. 28, 2009].
M. K. Industires (Gujarat India, http://www.soapstrips.com).
Sanipro Sanitary Products (Italy, http://www.sanipro.it).
Adhesives Research (Pennsylvania, http://12.4.33.51/news/apresmed.htm).
Solublon (Toyohashi Japan, http://www.solublon.com).
SPI Pharma (Delaware, http://www.spipharma.com).
Wenda (China, http://www.wenda.com).
MOVA Pharmaceutical and Kosmos (USA, http://www.icon-pr.com/news/news_print.cfm?inv_id=266-1).
Cima Labs, Inc. (Minnesota, http://www.cimalabs.com/).
Cardinal Health (Dublin, Ohio, http://spd.cardinal.com/).
Le Laboratoire du Bain (France, http://www.labodubain.com/).
Amerilab Technologies, Inc. (Minnesota, http://www.amerilabtech.com/).
Meguiar's Car Wash Strips: (Meguiar's Inc. California, http://www.automotivedigest.com/view_art.asp?articlesID=12414).
All Office Actions, U.S. Appl. No. 13/561,298.
All Office Actions, U.S. Appl. No. 15/665,886.
T. Hildebrand, P. Rüegsegger. Quantification of bone microarchitecture with the structure model index. Comp Meth Biomech Biomed Eng 1997; 1:15-23.
Vesterby, A.; Star vol. In Bone Research a Histomorphometric Analysis of Trabecular Bone Structure Using Vertical Sections; Anat Rec.; Feb. 1993; 235(2):325-334.
Briscoe et al. "The effects of hydrogen bonding upon the viscosity of aqueous poly(vinyl alcohol) solutions," from Polymer, 41 (2000), pp. 3851-3860.
PCT International Search Report, dated Jul. 14, 2015, 150 pages.
All final and non-final office actions for U.S. Appl. No. 14/690,593.
All final and non-final office actions for U.S. Appl. No. 15/665,886.
All final and non-final office actions for U.S. Appl. No. 16/431,028.
All final and non-final office actions for U.S. Appl. No. 16/431,115.
All final and non-final office actions for U.S. Appl. No. 16/577,120.
All final and non-final office actions for U.S. Appl. No. 16/589,504.
All final and non-final office actions for U.S. Appl. No. 16/912,876.
All final and non-final office actions for U.S. Appl. No. 16/918,292.
All final and non-final office actions for U.S. Appl. No. 29/672,822.
All final and non-final office actions for U.S. Appl. No. 29/676,338.
All final and non-final office actions for U.S. Appl. No. 29/707,807.
All final and non-final office actions for U.S. Appl. No. 29/707,809.
All final and non-final office actions for U.S. Appl. No. 29/728,687.
All final and non-final office actions for U.S. Appl. No. 29/728,688.
All final and non-final Office Actions, U.S. Appl. No. 15/979,961.
All final and non-final Office Actions, U.S. Appl. No. 15/981,096.
All Office Actions, U.S. Appl. No. 16/953,975.
All Office Actions, U.S. Appl. No. 17/070,205.
All Office Actions, U.S. Appl. No. 29/707,807.
All Office Actions, U.S. Appl. No. 29/766,885.
Design of "Detergent tablets" (Design Registration No. 000634142-0003), (No. of Publicly known information HH18274488), Registered Community Designs Bulletin, published by EUIPO on Jan. 9, 2007. (Copy not provided).
Design of "Detergent tablets" (Design Registration No. 000634142-0004), (No. of Publicly known information HH18274489), Registered Community Designs Bulletin, published by EUIPO on Jan. 9, 2007. (Copy not provided).
Design of "Soaps" accepted on Jul. 11, 1986, Publishing Office: Korean Intellectual Property Office (KIPO), Document Name: Design Gazette (Application No. 3019850005996), Publication Date: Jun. 9, 1986, (No. of Publicly known information: HG21900612). (Copy not provided).
Hexagon 4 ward soap mold, Soap, Cosmetics, New Silicon mold, Published on Sep. 29, 2016, Retrieved from Internet : http://candlebox.com/product/%EC%9C%A1%EA%B0%81-4%EA%B5%AC-%EB%B9%84%EB%88%84%EB%AA%B0 %EB%93%9C/2206/?page_4=3#none.
How Gemz work?, Gemz Hair Care, published on Oct. 1, 2018, retrieved on Apr. 27, 2021, retrieved from the Internet URL: https://www.youtube.com/watch?v=ts1waYk43g4.
https://www.craftcuts.com/hexagon-craft-shape. htmlHexagon wood cutouts, www.craftcuts.com, 1 page, reviewed as early as May 2018 (Year: 2018).
Kuraray: "Mowiol—Technical data sheet", Jun. 1, 2010 (Jun. 1, 2010),pp. 1-4, XP055119891, Retrieved from the Internet: URL:http://www.kuraray.eu/fileadmin/Downloads/mowiol/TDS_Mowiol_en_20110624.pdf [retrieved on May 23, 2014] (Copy not provided).
Michelle Villett, Why You Need a Sulfate-Free Shampoo, The Skincare Edit, updated date: Jan. 25, 2019, Original publication date: Feb. 22, 2016 (Year: 2016), 7 pages.
Okasaka et al., "Evaluation of Anionic Surfactants Effects on The Skin Barrier Function Based on Skin Permeability", Pharmaceutical Development and Technology, vol. 24, No. 1, Jan. 23, 2018, pp. 99-104.
Product Review: Gemz Solid Shampoo, Travel as Much, published on Mar. 19, 2019, retrieved on Apr. 27, 2021, retrieved from the Internet URL: https://travelasmuch.com/gemz-solid-shampoo-review/.
U.S. Appl. No. 29/728,688, filed Mar. 20, 2020, Douglas Charles Cook et al.
U.S. Appl. No. 29/728,687, filed Mar. 20, 2020, Douglas Charles Cook et al.
U.S. Appl. No. 29/707,809, filed Oct. 1, 2019, Sharonda Lee Crawford Washington et al.
U.S. Appl. No. 29/707,807, filed Oct. 1, 2019, Sharonda Lee Crawford Washington et al.
U.S. Appl. No. 29/766,885, filed Jan. 19, 2021, Wee Hau Tan et al.
All Office Actions; U.S. Appl. No. 17/357,119, filed Jun. 24, 2021.
Definition of Derivative by Merriam Webster Online Dictionary, Year, 2021.
Sahin st al. "A Study on Physical and Chemical Properties of Cellulose Paper immersed in Various Solvent Mixtures" International Journal Of Molecular Sciences, Jan. 2008; 9(1): 78-88.
Wermuth et al. Drug Discovery', "Drug Discovery Today, 2006", vol. 11 7/8, 348-354, Year 2006.
U.S. Appl. No. 29/819,499, filed Dec. 15, 2021 Sharonda Lee Crawford Washington et al.
All Office Actions: U.S. Patent Application U.S. Appl. No. 29/819,499 (Attorney Docket No. D-02805D0), filed on 12-1 May 2021 See Pair.
Color Keeper [online], [site visited Oct. 18, 2021]. Available from internet, URL: https://shopgemz.com/products/color-keeper?variant=130945950024348utm_source=google&utm_medium sepc&utm campaign=Shopping&gclid=CjOKCOjw5JSLBhCxARIsAHgO2SdAT7LTehpyxMiqTGtFETDalNuo9 cQSOpPwCmsmmdGAIYOUSekQEaAhOiEALw wcB (Year: 2021).
Paper Pieces Hexagons, announced 2018 [online], [site visited Oct. 14, 2021]. Available from internet, URLhttps://www.amazon.com/Paper-Pieces-HEX100OB-Hexagons-1200pe/dp/BO7DVYV2H N/ (Year: 2018).
Rounded hexagon shape, announced 2016 [online], [site visited Oct. 20, 2021], Available from internet, URL:https://www.vexels.com/png-svg/preview/139199/rounded-hexagon-shape (Year: 2016).
Dow, UCARETM Polymer LR-400, Technical Data Sheet, Downloaded in Mar. 2022, 4 pages.
Karen Duis et al., "Environmental fate and effects of water-soluble synthetic organic polymers used in cosmetic products", Environmental Sciences Europe, vol. 33, Article No. 21, Feb. 16, 2021,78 pages.

\* cited by examiner

COMPOSITIONS IN THE FORM OF DISSOLVABLE SOLID STRUCTURES

FIELD OF THE INVENTION

The present invention relates to compositions in the form of dissolvable solid structures. The dissolvable solid structures are formed using certain polymers that allow the structures to perform well for their intended use and allow for beneficial manufacturing conditions.

BACKGROUND OF THE INVENTION

Many personal care, fabric care and other consumer products in the market today are sold in liquid form. While widely used, liquid products often have tradeoffs in terms of packaging, storage, transportation, and convenience of use. Liquid consumer products typically are sold in bottles which add cost as well as packaging waste, much of which ends up in land-fills.

Dissolvable solid products have been disclosed, comprising a water-soluble polymeric structurant and a surfactant or other ingredients. Although existing dissolvable products provide good performance benefits to end users, the processes for making them can have less than optimal cost, rate of manufacture, and/or product variability parameters.

A need therefore still exists for dissolvable solid structures which perform well for their intended purpose and can be manufactured within desired cost and rate parameters. Additionally, it is desirable to improve the dissolving properties of the solid product to facilitate improved consumer satisfaction.

SUMMARY OF THE INVENTION

A Structure in the form of a porous dissolvable solid, comprising: (a) from about 1 wt % to about 95 wt % surfactant; and (b) from about 5 wt % to about 50 wt % of a vinyl acetate-vinyl alcohol copolymer, wherein said copolymer comprises not more than about 84% alcohol units.

A Structure in the form of a porous dissolvable solid that is an open celled foam, comprising: (a) from about 1 wt % to about 75 wt % surfactant; and (b) from about 10 wt % to about 50 wt % of a vinyl acetate-vinyl alcohol copolymer, wherein said copolymer comprises not more than about 84% alcohol units; wherein the foam Structure has a percent open cell of from about 80% to about 100%.

A Structure in the form of a porous dissolvable solid comprising a plurality of fibers comprising: (1) from about 1 wt % to about 95 wt % surfactant; and (2) from about 5 wt % to about 50 wt % of a vinyl acetate-vinyl alcohol copolymer, wherein said copolymer comprises not more than about 84% alcohol units.

A process for preparing a Structure in the form of a porous dissolvable solid that is an open celled foam, comprising the steps of: (a) preparing a pre-mixture comprising (1) from about 1 wt % to about 75 wt % surfactant, (2) from about 0.1 wt % to about 25 wt % of a vinyl acetate-vinyl alcohol copolymer, (3) not more than about 60 wt % water, and (4) optionally from about 0.1 wt % to about 25 plasticizer; wherein the pre-mixture: (i) has a viscosity at 70° C. of from about 1000 cps to about 100,000 cps and (ii) is heated to a temperature in the range of from about 60° C. to about 100° C.; (2) aerating the pre-mixture by introducing a gas into the pre-mixture to form a wet aerated mixture, wherein said wet aerated mixture comprises: (i) a density of from about 0.15 to about 0.65 g/ml and (ii) bubbles having a diameter of from about 5 to about 100 microns; (3) dosing the wet aerated mixture into individual cavities in a mold or as a continuous sheet; and (4) drying the wet aerated mixture by applying energy to heat the wet aerated mixture and evaporate water to provide a Structure; wherein the Structure has a percent open cell of from about 70% to about 100%.

A process for preparing a Structure in the form of a porous dissolvable solid comprising a significant number of fibers, comprising the steps of: (a) preparing a processing mixture comprising one or more vinyl acetate-vinyl-alcohol copolymers; one or more surfactants; and not more than about 60 wt % water; wherein the processing mixture has: a viscosity at 70° C. of from about 5,000 centipoise to about 150,000 centipoise; (b) fibrillating the processing mixture into fibers by a fluid film fibrillation process comprising a first pressurized gas stream directed against a liquid film of the processing mixture to form the fibers; (c) at least partially drying the fibers of the processing mixture by a second pressurized gas stream; (d) depositing the partially dry fibers on a surface to form a web of partially dry fibrous web structures; and (e) drying the partially dry fibrous web structure to a desired final moisture content.

DETAILED DESCRIPTION OF THE INVENTION

Definitions

Figure 1:
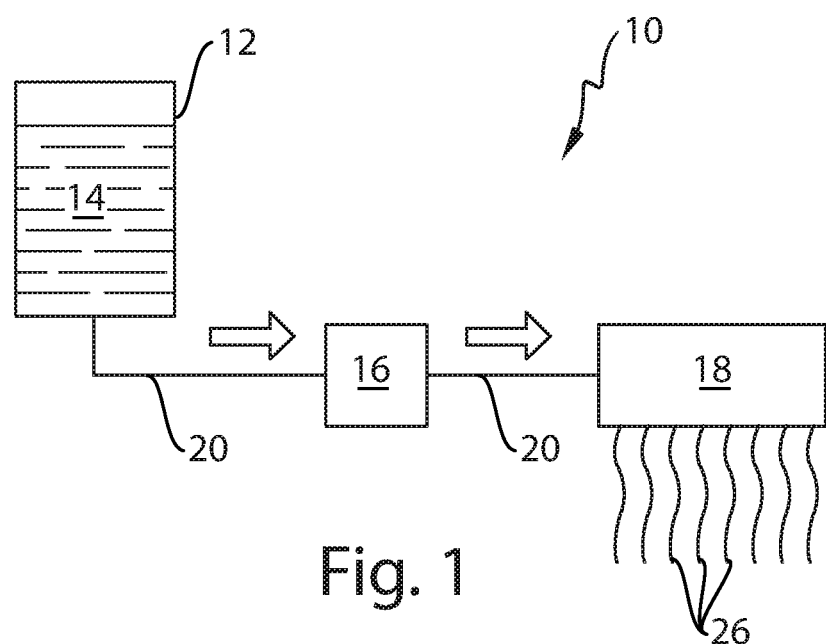
FIG. 1 is a schematic representation of an apparatus suitable for making fibers according to the present invention.

As used herein, the "average diameter" of the fibers making up a Structure is calculated as an arithmetic mean of diameters of all the dissolvable fibers in the sample measured. The relative standard deviation of fiber diameter is calculated by dividing the statistical standard deviation of the diameter by the average diameter of all the fibers in the measured sample. The method of measuring fiber diameter is described later in the disclosure.

As used herein, "dissolvable" means that the Structure meets the hand dissolution values discussed herein. The Structure has a hand dissolution value of from about 1 to about 30 strokes, in one embodiment from about 2 to about 25 strokes, in another embodiment from about 3 to about 20 strokes, and in still another embodiment from about 4 to about 15 strokes, as measured by the Hand Dissolution Method.

As used herein, "flexible" means a Structure meets the distance to maximum force values discussed herein.

As used herein "open celled foam" means a solid, interconnected, polymer-containing matrix that defines a network of spaces or cells that contain a gas, typically a gas such as air, without collapse of the foam structure during the drying process, thereby maintaining the physical strength and cohesiveness of the solid. The interconnectivity of the structure may be described by a Star Volume, a Structure Model Index (SMI) and a Percent Open Cell Content.

As used herein, "porous" means that the Structure has spaces, voids or interstices, (generally referred to herein as "pores") provided by the microscopic complex three-dimensional configuration, that provide channels, paths or passages through which a liquid can flow.

As used herein, "porosity" and "percent porosity" are used interchangeably and each refers to a measure of void volume of the Structure and is calculated as

[1−([basis weight of Structure]/[thickness of Structure×density of the bulk, dried material])]× 100% with the units adjusted so they cancel and multiplied by 100% to provide percent porosity.

The structure may be referred to herein as "the Structure" or "the Dissolvable Structure".

As used herein, "vinyl acetate-vinyl alcohol copolymer" (and "copolymer" when used in reference thereto) refers to a polymer of the following structure (I):

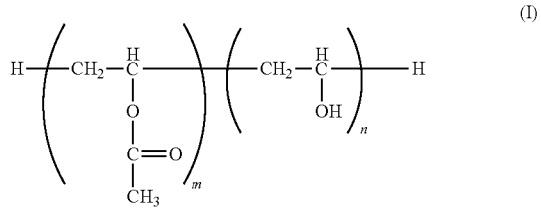

In structure (I), m and n are integers such that the copolymer has the degree of polymerization and percent alcohol characteristics described herein. For purposes of clarity, this use of the term "copolymer" is intended to convey that the partially hydrolyzed polyvinyl acetate of the present invention comprises vinyl alcohol and vinyl acetate units. As discussed below, the copolymer is routinely prepared by polymerizing vinyl acetate monomer followed by hydrolysis of some of the acetate groups to alcohol groups, as opposed to polymerization of vinyl acetate and vinyl alcohol monomer units (due in-part to the instability of vinyl alcohol).

As used herein, the articles including "a" and "an" when used in a claim, are understood to mean one or more of what is claimed or described.

As used herein, the terms "include," "includes," and "including," are meant to be non-limiting.

The methods disclosed in the Test Methods Section of the present application should be used to determine the respective values of the parameters of Applicants' inventions, including those discussed in the Dissolvable Structures—Physical Characteristics section below.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

I. Dissolvable Structures—Physical Characteristics

The Structures of the present invention are in the form of a dissolvable, porous solid composition wherein the porosity allows for liquid (e.g., water) flow during use such that the solid composition readily dissolves to provide a desired consumer experience. The porous nature of the Structure can be achieved in a variety of ways including, for example, forming an open celled foam or forming a fibrous structure.

In one embodiment, the percent porosity of the dissolvable solid Structure is at least about 25%, in another embodiment at least about 50%, in another embodiment at least about 60%, in another embodiment at least about 70% and in another embodiment at least about 80%. In one embodiment, the porosity of the dissolvable solid Structure is not more than about 99%, in another embodiment not more than about 98%, in another one embodiment not more than about 95%, and in another embodiment not more than about 90%. Porosity of a Structure is determined according to the procedure set forth in the definition of "porosity" above.

A range of effective sizes of pores can be accommodated. The pore size distribution through the Structure cross-section may be symmetric or asymmetric.

In one embodiment, the Structure will be flexible and have a distance to maximum force value of from about 6 mm to about 30 mm. In another embodiment the distance to maximum force value from about 7 mm to about 25 mm, in another embodiment from about 8 mm to about 20 mm, and in still another embodiment from about 9 mm to about 15 mm.

The Structure can be characterized in one aspect by its Specific Surface Area. In one embodiment, the Structure has a Specific Surface Area of from about 0.03 $m^2/g$ to about 0.25 $m^2/g$, in another embodiment from about 0.035 $m^2/g$ to about 0.22 $m^2/g$, in another embodiment from about 0.04 $m^2/g$ to about 0.19 $m^2/g$, and in still another embodiment from about 0.045 $m^2/g$ to about 0.16 $m^2/g$.

In one embodiment the Structure is a flat, flexible substrate in the form of a pad, a strip, or tape and having a thickness of from about 0.5 mm to about 10 mm, in one embodiment from about 1 mm to about 9 mm, in another embodiment from about 2 mm to about 8 mm, and in a further embodiment from about 3 mm to about 7 mm as measured by the below methodology. In another embodiment, the Structure is a sheet having a thickness from about 5 mm to about 6.5 mm. In another embodiment, two or more sheets are combined to form a Structure with a thickness of about 5 mm to about 10 mm.

In one embodiment, the Structure has a basis weight of from about 200 grams/$m^2$ to about 2,000 grams/$m^2$, in another embodiment from about 400 g/$m^2$ to about 1,200 g/$m^2$, in another embodiment from about 600 g/$m^2$ to about 2,000 g/$m^2$, and in still another embodiment from about 700 g/$m^2$ to about 1,500 g/$m^2$.

In one embodiment, the Structure has a dry density of from about 0.08 g/$cm^3$ to about 0.30 g/$cm^3$, in another embodiment from about 0.10 g/$cm^3$ to about 0.25 g/$cm^3$, and in another embodiment from about 0.12 g/$cm^3$ to about 0.20 g/$cm^3$.

For open cell foam Structures, the Structure has a Cell Wall Thickness. The Structure in one embodiment has a Cell Wall Thickness of from about 15 microns to about 55 microns, in another embodiment from about 20 microns to about 45 microns, and in another embodiment from about 25 microns to about 35 microns.

For open cell foam Structures, in one embodiment the Structure has a Star Volume of from about 1 $mm^3$ to about 90 $mm^3$, in another embodiment from about 5 $mm^3$ to about 80 $mm^3$, in another embodiment from about 10 $mm^3$ to about 70 $mm^3$, and in still another embodiment from about 15 $mm^3$ to about 60 $mm^3$. In one embodiment, the open cell foam Structure has a non-negative Structure Model Index of from about 0.0 to about 3.0, in one embodiment from about 0.5 to about 2.75, and in another embodiment from about 1.0 to about 2.50.

For open cell foam Structures, in one embodiment the Structure has a Percent Open Cell Content of from about 70% to 100%, in one embodiment from about 80% to about 97.5%, and in another embodiment from about 90% to about 95%.

For fibrous Structures, in one embodiment the Structure comprises a significant number of dissolvable fibers with an average diameter less than about 150 micron, in another embodiment less than about 100 micron, in an another embodiment less than about 10 micron, and in an yet another embodiment less than about 1 micron with a relative standard deviation of less than 100%, alternatively less than 80%, alternatively less than 60%, alternatively less than 50%, such as in the range of 10% to 50%, for example. As set forth herein, the significant number means at least 10% of all the dissolvable fibers, in another embodiment at least 25% of all the dissolvable fibers, in another embodiment at least 50% of all the dissolvable fibers, in yet another embodiment at least 75% of all the dissolvable fibers. In a particular embodiment, the significant number may be at least 99% of all the dissolvable fibers. In a further embodiment, at least 50% of all the dissolvable fibers may have an average diameter less than about 10 micron. The dissolvable fibers produced by the method of the present disclosure have a significant number of dissolvable fibers with an average diameter less than about 1 micron, or sub-micron fibers. In an embodiment, the article comprising Structure may have at least 25% of all the dissolvable fibers with an average diameter less than about 1 micron, in another embodiment at least 35% of all the dissolvable fibers with an average diameter less than about 1 micron, in another embodiment at least 50% of all the dissolvable fibers with an average diameter less than about 1 micron, and in yet another embodiment at least 75% of all the dissolvable fibers with an average diameter less than about 1 micron.

II. Dissolvable Structures—Compositional

The Structure (dried) of the present invention is in the form of a porous dissolvable solid, comprising: (a) from about 1 wt % to about 95 wt % surfactant; and (b) from about 5 wt % to about 50 wt % of a vinyl acetate-vinyl alcohol copolymer, wherein said copolymer comprises not more than about 84% alcohol units. In one embodiment, the Structure comprises from about 3 wt % to about 75 wt % surfactant; and in another embodiment from about 5 wt % to about 65 wt % surfactant. In one embodiment, the Structure comprises from about 10 wt % to about 50 wt % of the copolymer, in another embodiment from about 15 wt % to about 40 wt % of the copolymer, and in another embodiment from about 20 wt % to about 30 wt % of the copolymer.

A. Copolymer

The Structures of the present invention comprise at least one copolymer comprising vinyl acetate and vinyl alcohol units, wherein the copolymer comprises not more than about 84% alcohol units. While copolymers comprised of vinyl acetate and vinyl alcohol units have been used in the past to make good performing dissolvable structures (e.g., U.S. Pat. Nos. 8,466,099 and 8,461,090), the copolymers identified had a higher degree of vinyl alcohol content (i.e., higher degree of hydrolysis of the polyvinyl acetate starting polymer)—typically around 88%—than the copolymers used herein. Applicants have discovered that while the use of higher vinyl alcohol content copolymers are quite acceptable, there are surprising benefits associated with the lower alcohol content copolymers described herein. One important benefit is the lower alcohol copolymers allow for the use of significantly less water during production of the porous Structure. Among other things, this allows faster production rates resulting from less water introduction at the front end of the process and reduced drying time and energy after Structure formation. These benefits are reflected in the Examples section below.

In one embodiment, the copolymer comprises not more than about 82.5% alcohol units and in another embodiment not more than about 81% alcohol units. In one embodiment, the copolymer comprises from about 65% to about 84% alcohol units, in another embodiment from about 65% to about 82.5% alcohol units, and still another embodiment from about 70% to about 81% alcohol units. The percentage of alcohol units (i.e., the degree of hydrolysis) can be determined using standard titration chemistry techniques. One such procedure is described in ISO 15023-2:2003.

The degree of polymerization (average molecular weight) of the vinyl acetate-vinyl alcohol copolymer is measured using gel permeation chromatography (GPC). This form of chromatography utilizes size exclusion. Separation occurs through a column packed with porous beads. Smaller analytes spend more time in the pores and thus pass through the column more slowly. A detector measures the amount of polymer in the elution solvent as it is eluted. Reference herein to the molecular weight of the copolymer is weight average molecular weight ("Mw"). The Mw of the copolymer can vary widely, but in one embodiment the copolymer will have a Mw of from about 20,000 to about 500,000, in one embodiment from about 40,000 to about 400,000, in yet another embodiment from about 60,000 to about 300,000, and in still another embodiment from about 70,000 to about 200,000.

In one embodiment, the porous dissolvable Structures can be prepared by combining two or more vinyl acetate-vinyl alcohol copolymer materials described herein, wherein the copolymer materials differ with respect to either or both their degree of polymerization and/or their degree of hydrolysis.

The benefits identified can be achieved by using one copolymer described above, or it is possible to use two distinct vinyl acetate-vinyl alcohol copolymers.

In one embodiment, the porous dissolvable solid Structures can be prepared by combining a vinyl acetate-vinyl alcohol copolymer described herein with a polyvinylalcohol/polyvinylacetate having a higher degree of hydrolysis (e.g., about 88% hydrolyzed; "high hydrolysis polyvinylalcohol"). In such cases, the ratio (weight:weight) of the vinyl acetate-vinyl alcohol copolymer to high hydrolysis polyvinylalcohol will typically be from about 5:1 to about 1:5.

The vinyl acetate-vinyl alcohol copolymer useful in the present invention is readily prepared using well known chemistry. One such method is the hydrolysis of a starting polyvinyl ester (polyvinyl acetate; formed via polymerization of vinyl acetate monomer units) of the desired degree of polymerization with absolute alcohols (e.g., methanol) in the presence of catalytic amounts of alkali (e.g., sodium methoxide). In the hydrolysis of polyvinyl acetate to vinyl acetate-vinyl alcohol copolymer, products with different alcohol group contents can be obtained depending on production conditions. Hydrolysis conditions influence the structure of the vinyl acetate-vinyl alcohol copolymer formed. By varying catalyst concentration, reaction temperature, and the reaction time, the content of residual acetyl groups (i.e., unhydrolyzed acetyl groups) can be adjusted routinely. See, for example, *Polyvinyl Compounds, Others*, Ullmann's Encyclopedia of Industrial Chemistry, Vol. 29, p. 605-609 (2000). Vinyl acetate-vinyl alcohol copolymers are also available commercially, e.g. from Kuraray Europe GmbH.

B. Surfactants

The Structure comprises one or more surfactants suitable for application to the hair or skin. Surfactants suitable for use in the Structure include anionic surfactants, nonionic surfactants, cationic surfactants, zwitterionic surfactants, amphoteric surfactants, polymeric surfactants or combinations thereof. Although representative surfactants are described herein, the skilled artisan will recognize that other surfactants can be readily substituted and similar benefits can be derived from use of the vinyl acetate-vinyl alcohol copolymers described herein. Each patent described throughout this application is incorporated herein by reference to the extent each provides guidance regarding surfactants suitable for inclusion in the Structure.

In one embodiment, the Structure is a lathering dissolvable solid personal care product (dried) and comprises from about 23 wt % to about 75 wt % surfactant, in one embodiment from about 30 wt % to about 70 wt % surfactant, in another embodiment from about 40 wt % to about 65 wt % surfactant.

Suitable anionic surfactants include alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one embodiment, the anionic surfactant is sodium lauryl sulfate or sodium laureth sulfate.

In one embodiment, the anionic surfactant is at least one branched sulfate having the formula $CH_3—(CH_2)_z—CH(R^1)—CH_2—O—(CH_2CH(R^2)O)_y—SO_3M$; where z is from about 3 to about 14; $R^1$ represents H or a hydrocarbon radical comprising 1 to 4 carbon atoms, $R^2$ is H or CH3; $R^1$ and $R^2$ are not both H; y is 0 to about 7; the average value of y is about 1 when y is not =0; and M is a mono-valent or di-valent, positively-charged cation. Examples of mono-valent positively charged cations include ammonium, sodium, potassium, triethanolamine cation, and examples of di-valent positively charged cations include magnesium. For the foregoing branched sulfates, "average value" means that whereas the composition may comprise molecules having a value of y of other than 1, the average value of y all molecules in the composition is about 1.

Suitable amphoteric or zwitterionic surfactants include those which are known for use in shampoo or other cleansing products. Non limiting examples of suitable zwitterionic or amphoteric surfactants are described in U.S. Pat. Nos. 5,104,646 and 5,106,609, which are incorporated herein by reference in their entirety.

Suitable amphoteric surfactants include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants include cocoamphoacetate, cocoamphodiacetate, lauroamphoacetate, lauroamphodiacetate, and mixtures thereof.

Suitable zwitterionic surfactants include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

In another embodiment, the Structure is a substantially non-lathering dissolvable solid personal care product and comprises a) from about 0 wt % to about 10 wt % of an ionic (anionic, zwitterionic, cationic and mixtures thereof) surfactant, in one embodiment from about 0 wt % to about 5 wt % of an ionic surfactant, and in another embodiment from about 0 wt % to about 2.5 wt % anionic surfactant, and b) from about 1 wt % to about 50 wt % of a nonionic or polymeric surfactant, in one embodiment from about 5 wt % to about 45 wt % of a nonionic or polymeric surfactant, and in another embodiment from about 10 wt % to about 40 wt % of a nonionic or polymeric surfactant, and combinations thereof.

Suitable nonionic surfactants for use in the present invention include those described in McCutcheon's Detergents and Emulsifiers, North American edition (2010), Allured Publishing Corp., and McCutcheon's Functional Materials, North American edition (2010). Suitable nonionic surfactants for use in the Structure of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

In another embodiment, the nonionic surfactant is selected from sorbitan esters and alkoxylated derivatives of sorbitan esters including sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), sorbitan isostearate, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), all available from Uniqema, and combinations thereof.

Suitable polymeric surfactants include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

C. Optional Ingredients

The Structure (dried) optionally comprises from about 1 wt % to about 25 wt % plasticizer, in one embodiment from about 3 wt % to about 20 wt % plasticizer, in one embodiment from about 5 wt % to about 15 wt % plasticizer.

When present in the Structures, non-limiting examples of suitable plasticizing agents include polyols, copolyols, polycarboxylic acids, polyesters and dimethicone copolyols.

Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable plasticizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

EP 0283165 B1 discloses suitable plasticizers, including glycerol derivatives such as propoxylated glycerol.

The Structure may comprise other optional ingredients that are known for use or otherwise useful in compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1992.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, co-solvents or other additional solvents, and similar other materials.

Suitable conditioning agents include high melting point fatty compounds, silicone conditioning agents and cationic conditioning polymers. Suitable materials are discussed in US 2008/0019935, US 2008/0242584 and US 2006/0217288.

Non-limiting examples of product type embodiments for use by the Structure include hand cleansing substrates, hair shampoo or other hair treatment substrates, body cleansing substrates, shaving preparation substrates, fabric care substrate (softening), dish cleaning substrates, pet care substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and so forth.

III. Methods of Manufacture—Open Cell Foams

The use of low hydrolysis vinyl acetate-vinyl alcohol copolymer surprisingly allows for reduced water usage during Structure processing (when appropriately accounting for water introduced as the solvent for other materials). That is, the use of vinyl acetate-vinyl alcohol copolymer allows for processing starting with a higher % solids content pre-mixture. The % solids content is the summation of the weight percentages by weight of the total processing mixture of all of the solid, semi-solid and liquid components, excluding water and any obviously volatile materials such as low boiling alcohols. Applicants have also discovered that when making foam Structures using the vinyl acetate-vinyl alcohol copolymer in a relatively low water (not more than about 60 wt %) or high % solids (about 40% or greater) process, the dried foams exhibit improved integrity compared to foams made using high hydrolysis polymers. This provides in-use benefits including improved dissolution, as reflected in the examples section below.

A process for preparing a dissolvable open celled foam Structure comprising the steps of:
(a) preparing a pre-mixture comprising (1) from about 1 wt % to about 75 wt % surfactant, (2) from about 0.1 wt % to about 25 wt % of a vinyl acetate-vinyl alcohol copolymer, (3) not more than about 60 wt % water, and (4) optionally from about 0.1 wt % to about 25 plasticizer;
wherein the pre-mixture:
(i) has a viscosity at 70° C. of from about 1000 cps to about 100,000 cps; and
(ii) is heated to a temperature in the range of from about 60° C. to about 100° C.;
(b) aerating the pre-mixture by introducing a gas into the pre-mixture to form a wet aerated mixture, wherein said wet aerated mixture comprises:
(i) a density of from about 0.15 to about 0.65 g/ml; and
(ii) bubbles having a diameter of from about 5 to about 100 microns;
(c) dosing the wet aerated mixture into individual cavities in a mold or as a continuous sheet; and
(d) drying the wet aerated mixture by applying energy to heat the wet aerated mixture and evaporate water to provide a Structure;
wherein the Structure has a percent open cell of from about 70% to about 100%.

In one embodiment, the pre-mixture comprises from about 0.1 wt % to about 25 wt % of the pre-mixture of vinyl acetate-vinyl alcohol copolymer, in one embodiment from about 5 wt % to about 15 wt % copolymer, in one embodiment from about 7 wt % to about 10 wt % of the pre-mixture of the copolymer.

In one embodiment, the pre-mixture comprises from about 0.1 wt % to about 25 wt % of plasticizer, in one embodiment from about 1 wt % to 15 wt % plasticizer, in one embodiment from about 2 wt % to about 10 wt % plasticizer, and in another embodiment from about 2 wt % to about 4 wt % plasticizer.

A. Preparation of Pre-Mixture

The pre-mixture is generally prepared by mixing the solids of interest, including surfactant(s), vinyl acetate-vinyl alcohol copolymer, optional plasticizer and other optional ingredients. A benefit associated with use of the vinyl acetate-vinyl alcohol copolymer is that for open cell foam production, a relatively high solids content pre-mixture can be used. As discussed, high solids (i.e., reduced water) is of significant value as it allows for reduced water content on the front end of the making process and, accordingly, reduced time and energy is required to remove water to arrive at the desired dry Structure.

In one embodiment, the pre-mixture can be formed using a mechanical mixer. Mechanical mixers useful herein, include, but aren't limited to pitched blade turbines or MAXBLEND mixer (Sumitomo Heavy Industries).

For addition of the ingredients in the pre-mixture, it can be envisioned that the vinyl acetate-vinyl alcohol copolymer is ultimately dissolved in the presence of water, the surfactant(s), optional actives, plasticizer, and any other optional ingredients including step-wise processing via pre-mix portions of any combination of ingredients.

The pre-mixtures of the present invention comprise: at least about 40% solids, in one embodiment at least about 42%, in one embodiment at least about 44%, in another embodiment at least about 46%, and in another embodiment at least about 50%, by weight of the pre-mixture before drying.

In one embodiment, the viscosity of the pre-mixture is determined when the pre-mixture is heated to a temperature in the range of from about 60° C. to about 99° C. In one embodiment, the viscosity is measured at 1 sec$^{-1}$ and 70° C. In another embodiment, the viscosity of the pre-mixture is measured at ambient temperatures (25° C.).

When the pre-mixture is heated to a temperature in the range of between 60° C. and 99° C., it will have a viscosity of from about 1000 cps to about 20,000 cps, in one embodiment from about 2,000 cps to about 15,000cps, in one embodiment from about 3,000 cps to about 10,000 cps, and in another embodiment from about 4,000 cps to about 7,500 cps. The pre-mixture viscosity values are measured using a Brookfield RVDV-1 Prime Viscometer with CPE-41 cone and a shear rate of 1.0 reciprocal seconds for a period of 300 seconds.

B. Optional Continued Heating of Pre-Mixture

Optionally, the pre-mixture can be pre-heated immediately prior to the aeration process at above ambient temperature but below any temperatures that would cause degradation of the components. In one embodiment, the pre-mixture is kept at above about 40° C. and below about 99° C., in another embodiment above about 50° C. and below about 95° C., in another embodiment from about 60° C. and below about 90° C. In one embodiment, when the pre-mixture is heated to a temperature in the range of between 60° C. and 99° C., the pre-mixtures of the present invention have a viscosity of from about 1000 cps to about 20,000 cps, in one embodiment from about 2,000 cps to about 15,000cps, in one embodiment from about 3,000 cps to about 10,000 cps, and in another embodiment from about 4,000 cps to about 7,500 cps. In an additional embodiment, additional heat is applied during the aeration process to try and maintain an elevated temperature during the aeration. This can be accomplished via conductive heating from one or more surfaces, injection of steam or other processing means.

It is believed that the act of pre-heating the pre-mixture before the aeration step may provide a means for lowering the viscosity of pre-mixtures comprising higher percent solids content for improved introduction of bubbles into the mixture and formation of the desired Structure. Achieving higher percent solids content is desirable so as to reduce the energy requirements for drying. The increase of percent solids, and therefore conversely the decrease in water level content, and increase in viscosity is believed to affect the film drainage within the pre-mixture during the drying step. This film drainage and evaporation of water from the pre-mixture during drying is believed to assist the formation of the open celled structure of the Structure.

Pre-heating of the pre-mixture also allows for the manufacture of a fast dissolving Structure even when using a more viscous processing mixture. Without pre-heating, these viscous processing mixtures with higher percent solid levels normally produce Structures that are slow dissolving and that have predominately closed celled foams. However, the increased temperature during pre-heating causes drainage from the thin liquid film separating the bubbles outwards into the plateau borders of the open celled foam. This drainage generates openings between the bubbles which become the open cells of the Structure. The demonstrated ability to achieve such inter-connected open-celled foams of the Structures of the present invention is surprising.

In addition, a more viscous processing mixture results in Structures with low percent (%) shrinkage after the drying process while still maintaining fast dissolution rates. This is due to the fact that during the drying process, pre-mixtures with higher viscosities are able to mitigate the drainage and bubble rupture/collapse/coalescence that give rise to the shrinkage.

C. Aeration of Pre-Mixture

The aeration of the pre-mixture to form the wet aerated mixture is accomplished by introducing a gas into the pre-mixture in one embodiment by mechanical mixing energy, but also may be achieved via chemical means to form an aerated mixture. The aeration may be accomplished by any suitable mechanical processing means, including but not limited to: (i) batch tank aeration via mechanical mixing including planetary mixers or other suitable mixing vessels, (ii) semi-continuous or continuous aerators utilized in the food industry (pressurized and non-pressurized), or (iii) spray-drying the processing mixture in order to form aerated beads or particles that can be compressed such as in a mold with heat in order to form the porous solid.

In another embodiment, aeration with chemical foaming agents by in-situ gas formation (via chemical reaction of one or more ingredients, including formation of carbon dioxide ($CO_2$ (g)) by an effervescent system) can be used.

In a particular embodiment, it has been discovered that the Structure can be prepared within continuous pressurized aerators that are conventionally utilized in the foods industry in the production of marshmallows. Suitable continuous pressurized aerators include the Morton whisk (Morton Machine Co., Motherwell, Scotland), the Oakes continuous automatic mixer (E.T. Oakes Corporation, Hauppauge, N.Y.), the Fedco Continuous Mixer (The Peerless Group, Sidney, Ohio), the Mondo (Haas-Mondomix B. V., Netherlands), the Aeros (Aeros Industrial Equipment Co., Ltd., Guangdong Province, China), and the Preswhip (Hosokawa Micron Group, Osaka, Japan). Continuous mixers may work to homogenize or aerate slurry to produce highly uniform and stable foam structures with uniform bubble sizes. The unique design of the high shear rotor/stator mixing head may lead to uniform bubble sizes across the thickness of the initially wet aerated pre-mixture that is used to form the Structure (prior to drying).

Bubble size of the wet aerated mixture assists in achieving uniformity in the ultimate Structure. In one embodiment, the bubble size of the wet aerated mixture is from about 5 to about 100 microns and another embodiment, the bubble size is from about 20 microns to about 80 microns.

The uniformity of the bubble sizes causes the Structure to have consistent densities in the layers of the Structure. In one embodiment, the wet aerated mixture has a density from about 0.15 to about 0.50 g/mol., in one embodiment from about 0.20 to about 0.45 g/mol, in one embodiment from about 0.25 to about 0.40 g/mol, and in another embodiment from about 0.27 to about 0.38 g/mol.

D. Dosing

The wet aerated mixture can be dosed in a variety of ways prior to drying. For example, it can be dosed into individual cavities in a mold or as a continuous sheet. In one embodiment, the wet aerated mixture is dosed using a manifold-type device into individual cavities in a mold. Accurate dosing is needed to prevent over- or under-filling of the cavities. Ideally, the top surface will "self-level" and create a smooth, flat surface in the finished Structures; alternatively, scraping can be used to create a smooth, flat surface. Dosing can be performed with commercially available equipment that has been customized to deliver specific shapes and sizes. Suitable equipment can be provided by the E. T. Oakes Corporation, Hauppauge, N.Y., OKA-Spezialmaschinefabrik, Darmstadt, Germany, and Peerless Food Equipment, Sidney, Ohio. Product is dosed into molds that provide the desired shape and design for the finished Structure. Molds can be made from a variety of materials including metals, plastics, and composite materials. The use of flexible molds can assist with removal of the finished Structure from the molds after drying.

E. Drying

Energy is applied to the dosed, wet mixture to heat the foam and evaporate water. This energy can come from a variety of sources such as hot air, infra-red, radiative heat, etc. As the foam heats up, the air bubbles grow and start pressing against one another. This creates a pressure in the thin films that separate the air bubbles, causing these films to drain into the plateau border regions of the cellular structure. The drying rate and premix rheology is controlled to enable this film drainage, which in turn leads to the formation of an open celled foam structure during drying. This open celled foam structure provides good dissolution in the finished dry foam. If the drying rate and film rheology are not properly matched, the resulting structure may be a closed or partially closed cell foam which does not dissolve well. Drying can be performed using a variety of commercially available equipment, for example, impingement air dryer manufactured by Lincoln (a division of Manitowoc Foodservices) and Autobake Ovens and Baking Systems (Sydney, Australia). Drying via this method may result in a gradient of open cells pore sizes. The heat applied to the mold may result in uneven heating of the substrate, thus a pore gradient, with the largest pores forming on the side of the foam which is in contact with the mold. It will be understood that there may be some residual water remaining in the solid Structure after the drying process, but typically not more than about 10% by weight.

F. Conditioning

Under some drying conditions, there is an internal moisture gradient within the Structures when they exit the dryer. If this gradient is too large, and the center of the Structures are too wet, the quality of the Structures can be compromised in the Structure removal step. The Structures may be held for a period of time at controlled temperature and humidity conditions to allow the moisture gradient to equilibrate within the Structures.

G. Removal from Molds

When molds are used in the dosing step, a combination of mold inversion and suction can be used to remove Structures from the molds. Mold inversion is desirable because the porosity of the dried Structures is relatively high and can allow vacuum to pass through the Structures.

H. Minors Addition

Additional minor ingredients may be added to the Structures post-drying—in particular temperature sensitive materials such as perfume that might not withstand the drying conditions. These minors are added in a way that accurately doses the appropriate amount of material onto each Structure and provides an acceptable appearance on the finished Structure. Suitable methods include spray coating, roll coating and other coating technologies.

I. Other Foam Processing Considerations

Structures produced according to the molding process as described herein may, in some instances, form large pores towards the exterior surface of the Structure. Such Structures have a top and a bottom. The larger pores may be on one side of the Structure only, and may be only on the portion of the Structure which contacts a mold, when used. U.S. patent application Ser. No. 12/361,634, incorporated by reference herein, describes such Structures, as well as optional physical features that can be introduced to the foams by use of appropriate molds.

IV. Methods of Manufacture—Fibrous Substrates

When the Structure is in the form a fibrous web, it can be prepared by the process comprising the steps of:
(a) preparing a processing mixture comprising one or more vinyl acetate-vinyl-alcohol copolymers; one or more surfactants; and not more than about 60 wt % water; wherein the processing mixture has: a viscosity at 70° C. of from about 5,000 centipoise to about 150,000 centipoise;
(b) fibrillating the processing mixture into fibers by a fluid film fibrillation process comprising a first pressurized gas stream directed against a liquid film of the processing mixture to form the fibers;
(c) at least partially drying the fibers of the processing mixture by a second pressurized gas stream;
(d) depositing the partially dry fibers on a surface to form a web of partially dry fibrous web structures; and
(e) drying the partially dry fibrous web structure to a desired final moisture content.

Optionally, a surface resident coating can be applied to the Structure. The surface resident coating can be applied on the surface of fibers either when the fibers are in flight to the collector before forming a web, or after the web has been dried, as explained later in the Surface Resident Coating section.

A. Preparation of Processing Mixture

The processing mixture is generally prepared by dissolving the vinyl acetate-vinyl-alcohol copolymer in the presence of water, surfactant, optional plasticizer and other optional ingredients by heating followed by cooling. This can be accomplished by any suitable heated batch agitation system or via any suitable continuous system involving either single screw or twin screw extrusion or heat exchangers together with either high shear or static mixing. Any process can be envisioned such that the polymer is ultimately dissolved in the presence of water, the surfactant, the plasticizer, and other optional ingredients including stepwise processing via pre-mix portions of any combination of ingredients.

The pre-mixtures of the present invention comprise: at least about 40% solids, in one embodiment at least about 42%, in one embodiment at least about 44%, in another embodiment at least about 46%, and in another embodiment at least about 50%, by weight of the pre-mixture, before fiber formation; and have a viscosity of from about 5,000 centipoise to about 150,000 centipoise, in one embodiment from about 10,000 centipoise to about 125,000 centipoise, in another embodiment from about 15,000 centipoise to about 100,000 centipoise, in another embodiment from about 20,000 centipoise to about 75,000 centipoise, and in still another embodiment from about 25,000 centipoise to about 60,000 centipoise.

The wt % solids content is the summation of the weight percentages by weight of the total processing mixture of all of the solid, semi-solid and liquid components excluding water and any obviously volatile materials such as low boiling alcohols. The pre-mixture viscosity values are measured using a Brookfield RVDV-1 Prime Viscometer with CPE-41 cone and a shear rate of 1.0 reciprocal seconds for a period of 300 seconds.

B. Forming Fibers from the Processing Mixture

Fibers can be formed from many processes including, but not limited to, meltblowing processes, spunboding processes, bonded carded web processes, melt fibrillation and electrospinning and combinations thereof. The method of making the fibers can include a single step fibrillation process. Typical single step fibrillation processes used for thermoplastic polymers include melt blowing, melt film fibrillation, spun bonding, melt spinning in a typical spin/draw process, and combinations thereof. In one embodiment, the fibers can be formed in accordance with the processes described in U.S. Provisional Application No. 61/982,469, filed Apr. 22, 2014. In one embodiment, the fibers can be formed in accordance with the processes described in U.S. application Ser. No. 13/173,639, filed Jun. 30, 2011 by Glenn Jr., et al.

Spunbonded fibers refers to small diameter fibers which are formed by extruding molten thermoplastic material as filaments from a plurality of fine, usually circular capillaries of a spinneret with the diameter of the extruded filaments then being rapidly reduced as described in U.S. Pat. Nos. 3,692,618, 3,802,817, 3,338,992, 3,341,394, 3,502,763, 3,502,538, and 3,542,615.

Meltblown fibers mean fibers formed by extruding a molten thermoplastic material through a plurality of fine, usually circular, die capillaries as molten threads or filaments into converging high velocity gas streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed in U.S. Pat. No. 3,849,241.

Methods to produce fine fibers additionally comprise melt fibrillation and electrospinning Melt fibrillation is a general class of making fibers defined in that one or more polymers are molten and are extruded into many possible configurations (e.g., co-extrusion, homogeneous or bicomponent films or filaments) and then fibrillated or fiberized into filaments. Meltblowing is one such specific method (as described herein). Melt film fibrillation is another method that may be used to produce submicron fibers. A melt film is produced from the melt and then a fluid is used to form fibers from the melt film. Examples of this method comprise U.S. Pat. Nos. 6,315,806, 5,183,670, and 4,536,361, to Torobin et al., and U.S. Pat. Nos. 6,382,526, 6,520,425, and 6,695,992, to Reneker et al. and assigned to the University of Akron. The process according to Torobin uses one or an array of co-annular nozzles to form a fluid film which is fibrillated by high velocity air flowing inside this annular film. Other melt film fibrillation methods and systems are described in the U.S. Pat. Nos. 7,666,343 and 7,931,457 to Johnson, et al., U.S. Pat. No. 7,628,941, to Krause et al., and U.S. Pat. No. 7,722,347, to Krause, et al., and provide uniform and narrow fiber distribution, reduced or minimal fiber defects such as unfiberized polymer melt (generally called "shots"), fly, and dust, for example. These methods and systems further provide uniform nonwoven webs for absorbent hygiene articles.

Electrospinning is a commonly used method of producing sub-micron fibers. In this method, typically, a polymer is dissolved in a solvent and placed in a chamber sealed at one end with a small opening in a necked down portion at the other end. A high voltage potential is then applied between the polymer solution and a collector near the open end of the chamber. The production rates of this process are very slow and fibers are typically produced in small quantities. Another spinning technique for producing sub-micron fibers is solution or flash spinning which utilizes a solvent.

There is a difference between submicron diameter fibers made with electro-spinning versus those made with melt-fibrillation, namely the chemical composition. Electro-spun submicron fibers are made of generally soluble polymers of lower molecular weight than the fibers made by melt-fibrillation. Commercially-viable electro-spinning methods have been described in U.S. Pat. No. 7,585,437, to Jirsak et al., U.S. Pat. No. 6,713,011 to Chu et al., U.S. Pat. Publ. No. 2008/0237934, to Reneker et al, U.S. Pat. Publ. Nos. 2008/0277836 and 2008/0241297, to Park, and U.S. Pat. Publ. No. 2009/0148547, to Petras et al.

In one embodiment, a form of melt film fibrillation process is used. Generally, this process involves providing a thermoplastic polymeric melt, utilizing a pressurized gas stream to impinge on to the polymeric melt to form multiple fine fibers. Suitable melt film fibrillation methods are described in—for example, U.S. Pat. Nos. 4,536,361, 6,315,806, and 5,183,670 to Torobin; U.S. Pat. Nos. 6,382,526, 6,520,425, and 6,695,992, to Reneker; U.S. Pat. No. 7,666,343 to Johnson et al; U.S. Pat. No. 7,628,941, to Krause et al, and U.S. Pat. Publ. No. 2009/0295020, to Krause, et al, published on Dec. 3, 2009—all of which are incorporated herein as reference in their entirety. The melt film fibrillation methods can utilize different processing conditions. Torobin's and Reneker's method more specifically includes the steps of feeding the polymer melt into an annular column and forming a film at the exit of the annular column where a gas jet space is formed. A gas column then provides pressures on the inner circumference of the polymer film. When the polymer melt film exits the gas jet space, it is blown apart into many small fibers, including nanofibers, due to the expanding central gas.

While the melt film fibrillation methods, included as reference above, describe the use of thermoplastic polymer melt, it is surprising and non-intuitive that a film fibrillation method can be used for making fibers of the processing mixture fluids. Specifically, as used, a fluid film fibrillation process comprises a pressurized gas stream flowing within a confined gas passage, comprising an upstream converging wall surfaces and a downstream diverging wall surfaces into which the processing mixture fluid is introduced to provide an extruded processing mixture fluid film on a heated wall surface that is impinged by the gas stream flowing within the gas passage, effective to fibrillate the processing mixture fluid film into fibers. "Converging" means that the cross-sectional area decreases in the direction of gas flow; and "diverging" means that the cross-sectional area increases in the direction of gas flow. In one embodiment, the gas passage comprises a first, upstream section into which the gas enters from a supply end, a transition region, and a second, downstream section in which the gas flows to an exit end, wherein the transition region fluidly connects the first section to the second section, and the gas passage ends at the exit end of the second section. In a particular embodiment, the first section of the gas passage has a monotonically decreasing cross-sectional area from the supply end to the transition region, and the second section of the gas passage has a monotonically increasing cross-sectional area from the transition region to the exit end of the second section. At least one flowing processing mixture fluid stream is transmitted through at least one bounded passage which ends in at least one opening in at least one of the opposing heated walls. The processing mixture fluid is heated sufficiently in transit to make and keep it flowable until introduced into the gas passage. Each processing mixture fluid stream extrudes in the form of a film from each opening. Each extruded processing mixture fluid film joins with the gas stream and the processing mixture fluid film is fibrillated to form fibers exiting from the exit end of the second section of the gas passage. For purposes herein, "monotonically decreasing cross-sectional area" means "strictly decreasing cross-sectional area" from the upper inlet end to the lower end of the upstream nozzle section, and "monotonically increasing cross-sectional area" means "strictly increasing cross-sectional area" from the upper end to the exit end of the downstream section of the nozzle.

In a particular embodiment, each extruded processing mixture fluid film joins with the gas stream in the second section of the gas passage. The introduction of the processing mixture fluid in the second section of the nozzle system on a heated diverging support wall has been found to especially facilitate production of high quality fibers and resulting webs. In a further embodiment, the location where the extruded processing mixture fluid film joins with the gas in the second, downstream section in order to produce the best quality fibers and web depends on the type of gas, the nozzle geometry, including angles and transitions, and the pressure of the gas, and can be located in the upper half of the second section such as for low gas pressure conditions, and can be located in the lower, downstream half of the second section such as for high gas pressure conditions. In a particular embodiment, only one processing mixture fluid film forms on at least one of the heated walls, the gas pressure exceeds about 10 psi, and each processing mixture passage opening from which processing mixture film extrudes is located in a second, downstream half of the second section between the transition region and the exit end of the second section. It has been found that the second half of the downstream second section can provide an optimal gas velocity region where fluid film fibrillation is accomplished very efficiently, yielding higher quality fibrous product.

For the purposes of this disclosure, the bounded passages for pressurized gas and processing mixture fluid together will be referred as "nozzle" or "nozzle system". The nozzle may have bounded passages in a rectangular slot configuration or circular rounded configuration or elongated oval configuration or any configuration that would enable formation of one or more processing mixture fluid film(s) to be impinged by one or more pressurized gas streams. In particular, for a rectangular slot configuration, one or more pressurized gas streams may flow through a bounded rectangular slot passage to impinge on the processing mixture fluid film that forms on a rectangular wall surface to form the processing mixture fibers. In such rectangular slot configuration, the bounded passage for one or more processing mixture fluid may be circular rounded, or elongated oval, or rectangular slot, or any other shape.

Various processes and combinations of processes can be used to make the webs described herein. Fiber bursting, as disclosed in U.S. Pat. No. 7,326,663 by Sodemann et al. can be combined with fluid film fibrillation described herein on two separate beams on a single line. Various aspects of fiber bursting can be incorporated into fluid film fibrillation, such as producing fibers of different strengths and diameters to provide a desired combination of properties. Alternatively, aspects of fluid film fibrillation can be included in other fibrillation processes to increase the throughput rate by utilizing a fluid film fibrillation to form fibers. For example, the fluid film fibrillation process described herein could be modified to include a Laval nozzle to aid in drawing down the fibers. Drawing down can aid in further attenuation of the fibers.

The fibers described herein may also be produced by other spinning methods that typically yield submicron fibers. Such methods include electrospinning, electroblowing, and flash spinning In general, electrospinning employs an electrostatic force to draw a charged liquid polymeric formulation from a source to a collector. An electrostatic field is used to accelerate the liquid formulation from the source to the collector on which the fibers are collected. Suitable and non-limiting examples of electrospinning methods for making fibers as described herein, have been described in U.S. Pat. No. 7,585,437, to Jirsak et al., U.S. Pat. No. 6,713,011 to Chu et al., U.S. Pat. Publ. No. 2008/0237934, to Reneker et al, U.S. Pat. Publ. Nos. 2008/0277836 and 2008/0241297, to Park, U.S. Pat. Publ. No. 2009/0148547, to Petras et al, and U.S. Pat. Publ. No. 2006/0264130, to Karles, et al.

The electroblowing method comprises feeding a polymeric solution to a spinning nozzle to which a high voltage is applied while compressed gas is used to envelop the polymer solution in a forwarding gas stream as it exits the nozzle, and collecting the resulting nanofiber web on a grounded suction collector. Suitable and non-limiting examples of electroblowing methods, included herein as references in their entirety, comprise U.S. Pat. No. 7,582,247 to Armantrout et al, U.S. Pat. No. 7,585,451 to Bryner et al, U.S. Pat. No. 7,618,579 to Kim et al, U.S. Pat. Publ. No. 2006/0097431 to Hovanec, U.S. Pat. Publ. No. 2006/0012084 to Armantrout et al, and U.S. Pat. Publ. No. 2005/0073075 to Chu et al.

Another process to make fibers of the described herein is flash spinning, described in U.S. Pat. No. 3,081,519 to Blades and White (non-limiting example). In the flash spinning process, a polymeric solution at a temperature above the boiling point of the solvent and at a pressure at least autogenous is extruded into a medium of lower temperature and substantially lower pressure. The sudden boiling which occurs at this point causes either microcellular structures or fibrillated networks to form. The fibrillated materials tend to be formed when the pressure changes are most severe, or when more dilute solutions are used. Under these circumstances the vaporizing liquid within the extrudate forms bubbles, breaks through confining walls, and cools the extrudate, causing solid polymer to form therefrom. The resulting multifibrous strand has an internal fine structure or morphology characterized as a three-dimensional integral plexus consisting of a multitude of essentially longitudinally extended, interconnecting, random-length, fibrous elements, referred to as film-fibrils. These film-fibrils have the form of thin ribbons of a thickness, typically, less than 4 micron. Other suitable and non-limiting examples of the flash spinning process, included herein as references in their entirety, comprise U.S. Pat. Nos. 5,977,237 and 5,250,237 to Shin et al, U.S. Pat. No. 5,788,993 to Bryner et al, U.S. Pat. No. 6,638,470 to Schweiger, U.S. Pat. No. 4,260,565 to D'Amico et al, and U.S. Pat. No. 7,118,698 to Armantrout et al.

In a particular embodiment, the processing mixture may be spun into submicron (diameter less than about 1 micron) or micro-fiber (diameter ranging from about 1 micron to about 10 micron) using methods selected from the group of fluid film fibrillation, melt fibrillation, electrospinning, electroblowing, flash spinning, or combinations thereof.

The above methods, such as fluid film fibrillation, fiber bursting, electrospinning, or electroblowing, produce a significant number of dissolvable fibers with an average diameter less than about 1 micron, or sub-micron fibers. In an embodiment, the article comprising Structure may have at least 25% of all the dissolvable fibers with an average diameter less than about 1 micron, in one embodiment at least 35% of all the dissolvable fibers with an average diameter less than about 1 micron, in another embodiment at least 50% of all the dissolvable fibers with an average diameter less than about 1 micron, and in yet another embodiment at least 75% of all the dissolvable fibers with an average diameter less than about 1 micron. However, it may be desirable for a particular Structure produced by the methods of described herein be such that the methods are optimized to produce a significant number of dissolvable fibers with an average diameter less than about 150 micron, in one embodiment less than about 100 micron, in another embodiment less than about 10 micron, and yet another embodiment less than about 1 micron with a relative standard deviation of less than 100%, alternatively less than 80%, alternatively less than 60%, alternatively less than 50%, such as in the range of 10% to 50%, for example. As mentioned earlier in the present disclosure, the significant number means at least 10% of all the dissolvable fibers, in one embodiment at least 25% of all the dissolvable fibers, in another embodiment at least 50% of all the dissolvable fibers, yet another embodiment at least 75% of all the dissolvable fibers.

C. Forming the Fibrous Web Structure

The partially dry or dried to desired moisture content fibers of the processing mixture are laid down on a collector to form a web. The collector is typically a conveyor belt or a drum. The collector can be porous and vacuum may be applied to provide suction to aid fiber lay down on the collector. The distance from the orifice to the collector distance, commonly called die-to-collector distance (DCD), can be optimized for desired web properties. It may be desired to utilize more than one DCD used in a web, to change the DCD during production, or to have different beams with different DCDs. It may be desirable to form a web with different uniformities by changing the DCD. If the DCD is such that fibers are not sufficiently dried before depositing on the collector, the wet or insufficiently dry fibers may coalesce to form blobs or bundles that may not be desirable and would constitute as defects. Alternatively, it may be desirable for n Structure to have some or all fibers coalesce completely or partially, e.g., to have structural integrity. If the DCD is large and such that fibers are sufficiently dried, the fibers may entangle or stick to one another, but not coalesce, to form bundles or ropes that may not be desirable. Therefore, depending on the desired Structure, the DCD may be set to form fibrous web with desirable uniformity and sufficient dryness. Alternatively, the webs of desirable uniformity may be further dried to obtain moisture content desired in the Structure.

Additionally, the die-to-collector distance may be altered along with the vacuum underneath the collector to obtain desired density of the web. Generally, the shorter DCD and/or higher vacuum provide denser webs relative to the larger DCD. At shorter DCD and/or higher vacuum, the fibers tend to be "forced" together tightly by the fiberizing fluid jet and/or vacuum suction, while at the larger DCD and/or lower vacuum, the fibers stay fluffy and thus lower density. Therefore, depending on the desired Structure density, it may be desirable to optimize DCD and/or vacuum for uniformity, dryness, and density.

The fibrous webs of the processing mixture may be formed a desired shape or shapes including, but not limited to (i) depositing the fibrous web to specially designed molds comprising a non-interacting and non-stick surface including Teflon, metal, HDPE, polycarbonate, neoprene, rubber, LDPE, glass and the like; (ii) depositing the fibrous web into cavities imprinted in dry granular starch contained in a shallow tray, otherwise known as starch moulding forming technique; and (iii) depositing the fibrous web onto a continuous belt or screen comprising any non-interacting or non-stick material Teflon, metal, HDPE, polycarbonate, neoprene, rubber, LDPE, glass and the like which may be later stamped, cut, embossed or stored on a roll.

D. The Optional Drying of the Fibrous Web of the Processing Mixture

The optional drying of the formed partially dried fibrous web of the processing mixture may be accomplished by any suitable means including, but not limited to (a) multi-stage inline dryers using convection or through-air drying; (b) super-heated steam dryers; (c) drying room(s) including rooms with controlled temperature and pressure or atmospheric conditions; (d) ovens including non-convection or convection ovens with controlled temperature and optionally humidity; (e) truck/tray dryers, impingement ovens; (f) rotary ovens/dryers; (g) inline roasters; (h) rapid high heat transfer ovens and dryers; (i) dual plenum roasters, and (j) conveyor dryers.

Optional ingredients may be imparted during any of the above described four processing steps or even after the drying process. It will be understood that there may be some residual water remaining in the Structure after the optional drying process, but typically not more than about 10% by weight.

E. The Optional Preparing of the Surface Resident Coating Comprising the Active Agent The preparation of the surface resident coating comprising the active agent may include any suitable mechanical, chemical, or otherwise means to produce a particulate composition comprising the active agent(s) including any optional materials as described herein, or a coating from a fluid.

Optionally, the surface resident coating may comprise a water releasable matrix complex comprising active agent(s). In one embodiment, the water releasable matrix complexes comprising active agent(s) are prepared by spray drying wherein the active agent(s) is dispersed or emulsified within an aqueous composition comprising the dissolved matrix material under high shear (with optional emulsifying agents) and spray dried into a fine powder. The optional emulsifying agents can include gum arabic, specially modified starches, or other tensides as taught in the spray drying art (See Flavor Encapsulation, edited by Sara J. Risch and Gary A. Reineccius, pages 9, 45-54 (1988), which is incorporated herein by reference). Other known methods of manufacturing the water releasable matrix complexes comprising active agent(s) may include but are not limited to, fluid bed agglomeration, extrusion, cooling/crystallization methods and the use of phase transfer catalysts to promote interfacial polymerization. Alternatively, the active agent(s) can be adsorbed or absorbed into or combined with a water releasable matrix material that has been previously produced via a variety of mechanical mixing means (spray drying, paddle mixers, grinding, milling etc.). In one embodiment, the water releasable matrix material in either pellet or granular or other solid-based form (and comprising any minor impurities as supplied by the supplier including residual solvents and plasticizers) may be ground or milled into a fine powder in the presence of the active agent(s) via a variety of mechanical means, for instance in a grinder or hammer mill. Where the article has a particulate coating, the particle size is known to have a direct effect on the potential reactive surface area of the active agents and thereby has a substantial effect on how fast the active agent delivers the intended beneficial effect upon dilution with water. In this sense, the active agents with smaller particle sizes tend to give a faster and shorter lived effect, whereas the active agents with larger particle sizes tend to give a slower and longer lived effect. In one embodiment the surface resident coatings may have a particle size from about 1 μm to about 200 μm, in another embodiment from about 2 μm to about 100 μm, and in yet another embodiment from about 3 μm to about 50 μm.

In some embodiments, it is helpful to include inert fillers within the grinding process, for instance aluminum starch octenylsuccinate under the trade name DRY-FLO® PC and available from Akzo Nobel, at a level sufficient to improve the flow properties of the powder and to mitigate inter-particle sticking or agglomeration during powder production or handling. Other optional excipients or cosmetic actives, as described herein, can be incorporated during or after the powder preparation process, e.g., grinding, milling, blending, spray drying, etc. The resulting powder may also be blended with other inert powders, either of inert materials or other powder-active complexes, and including water absorbing powders as described herein.

In one embodiment, the active agents may be surface coated with non-hygroscopic solvents, anhydrous oils, and/or waxes as defined herein. This may include the steps of: (i) coating the water sensitive powder with the non-hydroscopic solvents, anhydrous oils, and/or waxes; (ii) reduction of the particle size of the active agent particulates, prior to, during, or after a coating is applied, by known mechanical means to a predetermined size or selected distribution of sizes; and (iii) blending the resulting coated particulates with other optional ingredients in particulate form. Alternatively, the coating of the non-hydroscopic solvents, anhydrous oils and/or waxes may be simultaneously applied to the other optional ingredients, in addition to the active agents, of the surface resident coating composition and with subsequent particle size reduction as per the procedure described above.

Where the coating is applied to the substrate as a fluid (such as by as a spray, a gel, or a cream coating), the fluid can be prepared prior to application onto the substrate or the fluid ingredients can be separately applied onto the substrate such as by two or more spray feed steams spraying separate components of the fluid onto the substrate.

F. The Optional Combining of the Surface Resident Coating Comprising the Active agents with the Structure Any suitable application method can be used to apply the surface resident coating comprising active agent to the article such that it forms a part of the article. For instance, the Structure can have a tacky surface by drying the Structure's surface to a specific water content before application of powder to facilitate the adherence of the surface resident coating comprising the active agents to the Structure. In one embodiment, the Structure is dried to a moisture content of from about 0.1 wt % to about 25%, in one embodiment from about 3% to about 25%, in another embodiment from about 5% to about 20% and in yet another embodiment from about 7% to about 15%. Alternatively, a previously dried Structure's surface can be made to reversibly absorb a desired level of atmospheric moisture prior to application of the powder within a controlled humidity environment for a specific period of time until equilibrium is achieved. In one embodiment, the humidity environment is controlled from about 20% to about 85% relative humidity; in another embodiment, from about 30% to about 75% relative humidity; and in yet another embodiment, from about 40% to about 60% relative humidity.

In another embodiment, the Structure is placed in a bag, tray, belt, or drum containing or otherwise exposed to the powder and agitated, rolled, brushed, vibrated or shaken to apply and distribute the powder, either in a batch or continuous production manner Other powder application methods may include powder sifters, electrostatic coating, tribo charging, fluidized beds, powder coating guns, corona guns, tumblers, electrostatic fluidized beds, electrostatic magnetic brushes, and/or powder spray booths. The surface resident coating comprising the active agent can be applied over portions or entire regions of the Structure's exterior surface, and can be applied in a manner to adorn, decorate, form a logo, design, etc.

The surface resident coating comprising active agents can be directly applied to fibers as they are being formed. The surface resident coating may adhere and/or get embedded on the surface of partially or desirably dried fibers. Suitable and non-limiting examples of applying surface resident coatings on fibers, included as references herein in their entirety, comprise U.S. Pat. Nos. 7,291,300 and 7,267,789 to Chhabra and Isele, and U.S. Pat. Nos. 6,494,974 and 6,319,342 to Riddell.

Where the coating is applied to the substrate in a fluid, it is preferable that if water is present in the fluid that the water is not sufficient to cause the substrate to undesirable dissolve. In preferred embodiments, the active agent(s) to be applied as an adsorbed thin coating is an anhydrous or substantially anhydrous oil. Other non-water solvents, such as organic solvents which do not cause the substrate to dissolve may also be used. Any suitable application method can be used to apply the active agent(s) in liquid form to the article such that it forms a surface-resident coating that is adsorbed to at least a portion of the solid/air interface of the article as a thin film. For instance, it can be sprayed, spread, dropped, printed, sandwiched between different articles or different portions of the same article, layered, injected, rolled on, or dipped. The active agent(s) can be applied over portions or entire regions of the article's exterior surface, and can be applied in a manner to adorn, decorate, form a logo, design, etc.

To obtain the desired fibrous Structure, the methods described herein may be combined. In an embodiment, the dissolvable fibers produced from one or more methods described herein may be mixed homogenously or in layers to have desired performance for the Structures described herein. Different methods described herein may be optimized to produce dissolvable fibers with substantially or otherwise different actives or use of a particular surfactant, extensional rheology modifier, plasticizer, polymer structurant water soluble polymer, or other optional or required ingredients. Still alternatively, different methods may be optimized to produce dissolvable fibers with different dissolution rates and/or different diameter. In a particular embodiment, the submicron dissolvable fibers produced by the fluid film fibrillation method may be mixed homogenously or in layers with the dissolvable fibers produced from fiber bursting or electrospinning or electroblowing method. In some embodiments, the dissolvable fibrous web structure produced by one or more methods, or even by the same method, may have a mixture of fibers that have substantially or marginally different fiber diameter distributions, compositions, surface resident coatings, dissolution rates, or combinations thereof. In case of an embodiment with a mixture of fibers that have significantly different fiber diameter distributions, the average diameter of fibers from the different fiber diameter distributions may range from about 0.1 micron to about 150 micron.

Homogenous mixture of fibers produced by one or more methods may have a performance advantage in optimizing, such as slowing or speeding up the dissolution rates for a particular embodiment Structure, e.g., for controlled or timed release of actives. The layering of fibers produced by one or more methods may have a performance advantage in varying the dissolution rate during the use of the Structure, for example, certain actives or ingredients of the composition may need to be delivered at different times during the usage of the Structure, such as timed release of surfactant and conditioner, or detergent and bleach, or detergent and softener, and so forth. Other advantages of mixing dissolvable fibers produced by the methods described herein may be specific to a particular Structure.

The homogenous mixing of fibers may be achieved during the forming of fibrous web structure, such as via use of different nozzles or blocks or beams of nozzles employing different methods in a simultaneous fashion, for example, nozzles arranged in a staggered configuration in two-(planar) and/or three dimensions, or simply dissolvable fiber streams coming in at various angles with fibers depositing onto the collector. Examples of homogenously mixing fibers using an array of plurality of fiber-producing nozzles employing fluid film fibrillation process are provided by Torobin in U.S. Pat. Nos. 6,183,670 and 6,315,806. The layering of fibers may be achieved during the forming of the fibrous web structure, such as nozzles of different methods arranged adjacent to one another or following one another separated by a particular distance along the machine direction (the direction conveyor belt is moving) in a continuous manner, for example, nozzles in separate blocks or beams that are arranged in line along the machine direction. Alternatively, the dissolvable fibrous web structures produced by different methods may be combined offline in batches by layering over another before or after drying to desired moisture content. When combined as layers, one or more dissolvable fibrous web structures, produced by one or more methods, may have fibers that are substantially different in different layers of the dissolvable fibrous webs. The difference in fibers may be in substantially or marginally different diameter distributions, compositions, surface resident coatings, dissolution rates, porosities, or combinations thereof. For example, the substantially different fiber diameter distribution of fibers in different layers may have average diameters ranging from about 0.1 micron to about 150 micron.

The Structure may comprise one or more dissolvable fibrous web structures combined (e.g., laminated, layered, sandwiched, embedded, and so forth) with one or more other types of web structures and/or Structures. Suitable and non-limiting examples of Structures that may be combined include U.S. Pat. Publ. No. 2004/0048759 to Ribble et al, U.S. Pat. No. 6,106,849 to Malkan et al, U.S. Pat. Publ. No. 2007/0225388 to Cooper et al, U.S. Pat. No. 5,457,895 to Kearney et al, U.S. Pat. Publ. No. 2009/0232873 to Glenn et al, U.S. Pat. No. 7,196,026 and PCT Appl. No. WO2001/47567 to Di Luccio et al, PCT Application No. WO2007/093558 to Simon et al, U.S. Pat. App. Publication Nos. 2008/0035174, 2008/0269095, 2007/0128256, and 2007/0134304 to Auburn-Sonneville et al, U.S. Pat. App. Publication No. 2006/0159730 to Simon, and U.S. Pat. Nos. 5,342,335 and 5,445,785 to Rhim

V. Methods of Use

The compositions described herein may be used for cleaning and/or treating hair, hair follicles, skin, teeth, the oral cavity, fabric and hard surfaces. The method for treating these consumer substrates may comprise the steps of: a) applying an effective amount of the Structure to the hand, b) wetting the Structure with water to dissolve the solid, c) applying the dissolved material to the target consumer substrate such as to clean or treat it, and d) rinsing the diluted treatment composition from the consumer substrate. These steps can be repeated as many times as desired to achieve the desired cleansing and or treatment benefit. Alternatively, the Structure can be inserted into a machine (such as a washing machine or dish washer) in a unit dose manner and the machine can perform the dissolution, treating and rinsing steps.

According to yet another embodiment, a method is provided for providing a benefit to hair, hair follicles, skin, teeth, the oral cavity, fabric and hard surfaces, comprising the step of applying a composition according to the first embodiment to these target consumer substrates in need of regulating.

Described herein is a method for regulating the condition of hair, hair follicles, skin, teeth, the oral cavity, fabric and hard surfaces, comprising the step of applying one or more compositions described herein to these target consumer substrates in need of regulation.

The amount of the composition applied, the frequency of application and the period of use will vary widely depending upon the purpose of application, the level of components of a given composition and the level of regulation desired. For example, when the composition is applied for whole body or hair treatment, effective amounts generally range from about 0.5 grams to about 10 grams, in one embodiment from about 1.0 grams to about 5 grams, and in another embodiment from about 1.5 grams to about 3 grams.

VI. Product Types and Articles of Commerce

Non-limiting examples of product embodiments that utilize the Structures include hand cleansing substrates, teeth cleaning or treating substrates, oral cavity substrates, hair shampoo or other hair treatment substrates, body cleansing substrates, shaving preparation substrates, fabric care substrates (including, e.g., softening), dish cleaning substrates, pet care substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and so forth.

Described herein is an article of commerce comprising one or more Structures described herein, and a communication directing a consumer to dissolve the Structure and apply the dissolved mixture to hair, hair follicles, skin, teeth, the oral cavity, fabric and hard surfaces to produce a cleansing effect, a benefit to the target consumer substrate, a rapidly lathering foam, a rapidly rinsing foam, a clean rinsing foam, and combinations thereof. The communication may be printed material attached directly or indirectly to packaging that contains the Structure or on the Structure itself. Alternatively, the communication may be an electronic or a broadcast message that is associated with the article of manufacture. Alternatively, the communication may describe at least one possible use, capability, distinguishing feature and/or property of the article of manufacture.

VII. Test Methods

A. Distance to Maximum Force Method

Measured via a Rupture Method on a Texture Analyzer using a TA-57R cylindrical probe with Texture Exponent 32 Software. The Structure should have a thickness of between 4 to 7 mm and cut in a circle with a diameter of at least 7 mm for this method; or carefully cut or stacked to be within this overall thickness and diameter range. The porous solid sample is carefully mounted on top of the cylinder with four screws mounted on top with the top lid affixed in place on top of the sample. There is a hole in the center of the cylinder and its lid which allows the probe to pass through and stretch the sample. The sample is measured with a pre-test speed of 1 mm per second, a test speed of 2 mm per second and a post test speed of 3 mm per second over a total distance of 30 mm The distance to maximum force is recorded.

B. Hand Dissolution Method

One Structure, with dimensions of approximately 43 mm×43 mm×4-6 mm, is placed in the palm of the hand while wearing nitrile gloves. 7.5 cm$^3$ of from about 30° C. to about 35° C. tap water is quickly applied to the product via syringe. Using a circular motion, palms of hands are rubbed together 2 strokes at a time until dissolution occurs (up to 30 strokes). The hand dissolution value is reported as the number of strokes it takes for complete dissolution or as 30 strokes as the maximum.

C. Lather Profile: Lather Volume

The Structure provides a lather profile as described hereafter. The lather volume assessment is performed on 15g/10 inch flat Oriental virgin hair switches that have been treated with 0.098g of artificial liquid sebum [10-22% olive oil, 18-20% coconut oil, 18-20% oleic acid, 5-9% lanolin, 5-9% squalene, 3-6% palmitic acid, 3-6% paraffin oil, 3-6% dodecane, 1-4% stearic acid, 1-4% cholesterol, 1-4% coconut fatty acid, 18-20% choleth-24]. The hair switch is rinsed with 9-11 grain, 100° F. water at 1.5 gallons/min for 20 seconds with a shower nozzle. For testing the liquid control products, 0.75 cm$^3$ of liquid product are applied to the center of the switch, the lower portion of hair on the switch is then rubbed over the product on the hair 10 times in a circular motion, followed by 40 strokes back and forth (a total of 80 strokes). Lather speed is recorded as the number of strokes when the first lather is obviously generated during the 80 strokes. Lather from operator's gloves is transferred to a graduated cylinder with a 3.5 cm inside diameter and with total capacities of either 70 ml, 110 ml, or 140 ml depending on the total amount of lather generated (height modification of standard sized graduated cylinders via a glass shop). Lather from hair is gathered using one downward stroke on the switch with a tight grip and is also placed into the cylinder. Total lather volume is recorded in milliliters. Three runs per test sample are performed and the mean of the three values is calculated. When testing the Structure, 0.20+/−0.01 grams of product are weighed with the aid of scissors if required and applied to the switch and then 2 cm$^3$ of additional water are added to the product via syringe. The lathering technique is then performed as described for liquid products after a 10 second waiting time.

As used herein, the terms "substantially non-lathering" and "non-lathering" are used to mean a lather volume of from 0 ml to 20 ml.

D. Open Cell Foam—Cell Wall Thickness/Pore Size

For open cell foam Structures, the Structure has a Cell Wall Thickness. The Cell Wall Thickness is computed from the scanned images via a micro computed tomography system (μCT80, SN 06071200, Scanco Medical AG) as described herein. The Cell Wall Thickness is determined according to the method defined for the measurement of Trabecular Thickness using Scanco Medical's Bone Trabecular Morphometry evaluation.

The Cell wall thickness and spacing is calculated as the trabecular thickness and trabecular spacing using the ImageJ program with BoneJ plugin. ImageJ is a public domain, Java-based image-processing program developed at the National Institutes of Health and is available for download at http://rsb.info.nih.gov/ij. Information on the development of BoneJ can be found in the following article: Doube M, Kłosowski M M, Arganda-Carreras I, Cordeliéres F, Dougherty R P, Jackson J, Schmid B, Hutchinson J R, Shefelbine S J. (2010) BoneJ: free and extensible bone image analysis in ImageJ B*one* 47:1076-9. doi: 10.1016/j.bone.2010.08.023.

BoneJ is an open source/free software plugin for ImageJ to facilitate calculations commonly used in trabecular bone analysis. Images obtained from the Scanco µCT50 have a pixel size equal to 0.002 mm. These images are subsampled to 0.004 mm sized pixels for easier data handling and prepared as a series of binary images (slices) using the program, Aviso Standard v6.3.1. Once the binary images are created, they are exported as a series of 2D TIFF images. The images are then loaded into ImageJ using the "Import Image Sequence" function. They are then analyzed using the BoneJ "Thickness" measurement option. The resulting data has units of pixels and are converted to millimeters by multiplying each data by 0.004.

Weighted Radius can be used to measure the pore diameter. The weighted radius is calculated from the three dimensional data from the mCT. The mCT can be treated as a stack of two dimensional images in the height direction. Estimating the change in bubble diameter from slice to slice is done using the following steps. Each image (or slice) is converted to a binary image by using an appropriate threshold which separates formula material from void space. Each slice is 3.8 microns. The Structure is assigned the bright foreground pixels (value of one) and void space is dark background pixels (value of zero). For each binary slice, the Euclidean distance transform is calculated. The Euclidean distance transform assigns each dark pixel a new value based on the distance to the nearest foreground pixel. Most image processing packages, such as MATLAB, offer the Euclidean distance transform as a standard image processing method. The algorithm can be designed to execute very quickly. The average of the assigned Euclidean distance values multiplied by 3 is used as a surrogate for void bubble diameter and plotted with respect to height (this value is the weighted radius). This weighted radius is then multiplied by two to arrive at the pore diameter. This method is further described in the article Maurer, Calvin, Rensheng Qi, and Vijay Raghavan, "A Linear Time Algorithm for Computing Exact Euclidean Distance Transforms of Binary Images in Arbitrary Dimensions," IEEE Transactions on Pattern Analysis and Machine Intelligence, Vol. 25, No. 2, February 2003, pp. 265-270.

E. Specific Surface Area

The Specific Surface Area is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the combined weight of the degassed sample and the sample tube. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved. Samples may then be analyzed using an ASAP 2420 with krypton gas adsorption. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde Orr and Paul Webb.

F. Thickness

The thickness of the Structure is obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1 in. diameter platen weighing about 32 grams, which measures thickness at an application pressure of about 0.09 psi (6.32 g/cm$^2$).

The thickness of the Structure is measured by raising the platen, placing a section of the sample substrate on the stand beneath the platen, carefully lowering the platen to contact the sample substrate, releasing the platen, and measuring the thickness of the sample substrate in millimeters on the digital readout. The sample substrate should be fully extended to all edges of the platen to make sure thickness is measured at the lowest possible surface pressure, except for the case of more rigid substrates which are not flat. For more rigid substrates which are not completely flat, a flat edge of the substrate is measured using only one portion of the platen impinging on the flat portion of the substrate.

G. Basis Weight

The Basis Weight of a Structure is calculated as the weight of the Structure component per area of the component (grams/m$^2$). The area is calculated as the projected area onto a flat surface perpendicular to the outer edges of the porous solid. For a flat object, the area is thus computed based on the area enclosed within the outer perimeter of the sample. For a spherical object, the area is thus computed based on the average diameter as $3.14 \times (diameter/2)^2$. For a cylindrical object, the area is thus computed based on the average diameter and average length as diameter×length. For an irregularly shaped three dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (shaded-in for contrast) including a scale and using image analysis techniques.

H. Dry Density

The dry density of a Structure is determined by the equation: Calculated Density=Basis Weight of porous solid/(Porous Solid Thickness×1,000). The Basis Weight and Thickness of the dissolvable porous solid are determined in accordance with the methodologies described herein.

Scanning Electron Microscope (SEM) Imaging:

Representative sections are cut from the sponge with a clean razor blade and mounted with the cut face up on a standard cryo-SEM stub. Samples are secured onto the stub with carbon tape and silver paint. Samples are imaged using an Hitachi S-4700 FE-SEM fitted with a Gatan Alto 2500 cryo stage. Samples are cooled to −95 dC before imaging in the microscope. Samples are lightly coated with Platinum to reduce charging. Representative images are collected at 2 kV, 20 uA extraction voltage, ultra high resolution mode using the lower secondary electron detector. Long working distances are used to allow the entire sample to be imaged in one frame.

I. Open Cell Foam Structures—Star Volume and Structure Model Index

For open cell foam Structures, to measure the cell interconnectivity via the Star Volume and the Structure Model Index, disk-like samples, approximately 4 cm in diameter and 3 to 7 mm high, are scanned using a micro computed tomography system (μCT80, SN 06071200, Scanco Medical AG). Each sample is imaged while sitting flat on the bottom of a cylindrical tube. Image acquisition parameters are 45 kVp, 177 μA, 51.2 mm field of view, 800 ms integration time, 1000 projections. The number of slices is adjusted to cover the height of the sample. The reconstructed data set consisted of a stack of images, each 2048×2048 pixels, with an isotropic resolution of 25 μm. For data analysis, a volume of interest is selected to be fully within the sample, avoiding the surface region. A typical volume of interest is 1028× 772×98 voxels.

Structure Model Index (SMI) is measured using Scanco Medical's Bone Trabecular Morphometry evaluation with a threshold of 17. With this index the structural appearance of trabecular bone is quantified (see T. Hildebrand, P. Rüegsegger. Quantification of bone microarchitecture with the structure model index. *Comp Meth Biomech Biomed Eng* 1997; 1:15-23). The triangulated surface is dilated in normal direction by an infinitesimal amount, and the new bone surface and volume is calculated. By this, the derivative of the bone surface (dBS/dr) can be determined. The SMI is then represented by the equation:

$$SMI = 6 \cdot \frac{BV \cdot \frac{dBS}{dr}}{BS^2}$$

SMI relates to the convexity of the structure to a model type. Ideal (flat) plates have an SMI of 0 (no surface change with dilation of the plates), whereas ideal cylindrical rods have an SMI of 3 (linear increase in surface with dilation of rods). Round spheres have an SMI of 4. Concave structure gives negative dBS/dr, resulting in negative SMI values. Artificial boundaries at the edge of the volume of interest are not included in the calculation and thus suppressed.

In addition to the Scanco Medical Analysis, Star Volume measurements are made. Star Volume is a measure of the "openness" of the void space in a two phase structure. By choosing a random uniformly distributed set of points in the phase of interest (in this case the phase of interest is the void space or air), lines can be extended in random directions from each of these points. The lines are extended until they touch the foreground phase. The length of each of these lines is then recorded. The random points have a sampling of 10 in each direction (x/y/z) and at each point 10 random angles are chosen. If the line extends to the border of the ROI of interest that line is discarded (only accept lines that actually intersect with the foreground phase). The final equation is based upon the research entitled *Star Volume In Bone Research A Histomorphometric Analysis Of Trabecular Bone Structure Using Vertical Sections;* Vesterby, A.; Anat Rec.; 1993 February; 235(2):325-334.:

$$\text{Star Volume} = \frac{4}{3}\pi \cdot \frac{\sum dist^3}{N}$$

where "dist" is the individual distances and N is the number of lines examined

J. Open Cell Foam Structures—Open Cell Content

For open cell foam Structures, the Percent Open Cell Content is measured via gas pycnometry. Gas pycnometry is a common analytical technique that uses a gas displacement method to measure volume accurately. Inert gases, such as helium or nitrogen, are used as the displacement medium. The sample of the Structure is sealed in the instrument compartment of known volume, the appropriate inert gas is admitted, and then expanded into another precision internal volume. The pressure before and after expansion is measured and used to compute the sample Structure volume. Dividing this volume into the sample Structure weight gives the gas displacement density.

K. Fibrous Structures—Fiber Diameter

For fibrous Structures, the diameter of dissolvable fibers in a sample of a web is determined by using a Scanning Electron Microscope (SEM) or an Optical Microscope and image analysis software. A magnification of 200 to 10,000 times is chosen such that the fibers are suitably enlarged for measurement. When using the SEM, the samples are sputtered with gold or a palladium compound to avoid electric charging and vibrations of the fibers in the electron beam. A manual procedure for determining the fiber diameters is used from the image (on monitor screen) taken with the SEM or the optical microscope. Using a mouse and a cursor tool, the edge of a randomly selected fiber is sought and then measured across its width (i.e., perpendicular to fiber direction at that point) to the other edge of the fiber. A scaled and calibrated image analysis tool provides the scaling to get actual reading in microns (μm). Several fibers are thus randomly selected across the sample of the web using the SEM or the optical microscope. At least two specimens from the web (or web inside a product) are cut and tested in this manner Altogether at least 100 such measurements are made and then all data are recorded for statistic analysis. The recorded data are used to calculate average (mean) of the fiber diameters, standard deviation of the fiber diameters, and median of the fiber diameters. Another useful statistic is the calculation of the amount of the population of fibers that is below a certain upper limit. To determine this statistic, the software is programmed to count how many results of the fiber diameters are below an upper limit and that count (divided by total number of data and multiplied by 100%) is reported in percent as percent below the upper limit, such as percent below 1 micron diameter or %-submicron, for example. We denote the measured diameter (in microns) of an individual circular fiber as $d_i$.

In case the fibers have non-circular cross-sections, the measurement of the fiber diameter is determined as and set equal to the hydraulic diameter which is four times the cross-sectional area of the fiber divided by the perimeter of the cross of the fiber (outer perimeter in case of hollow fibers). The number-average diameter, alternatively average diameter is calculated as, $d_{num}$ $$\frac{\sum_{i=1}^{n} d_i}{n}$$

VII. Non-Limiting Examples

A. Non-limiting Examples of Fibrous Structures

Figure 2:
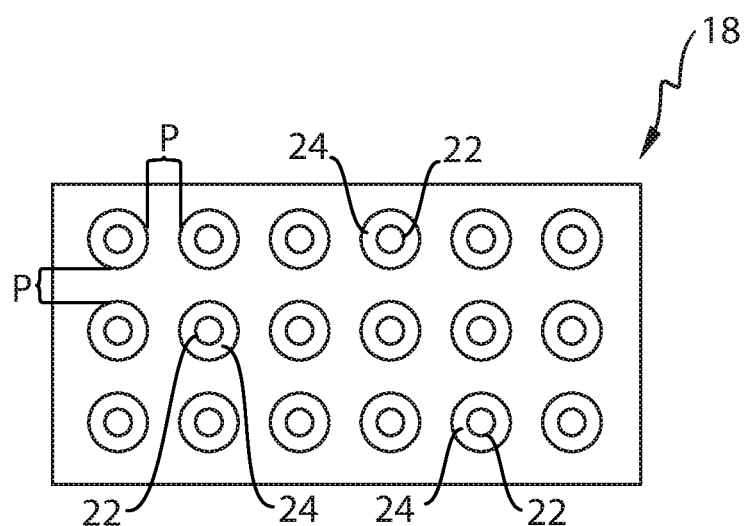
FIG. 2 is a schematic representation of a die suitable for spinning fibers according to the present invention.

Fibers according to the present invention are produced by using a small-scale apparatus 10, a schematic representation of which is shown in FIGS. 1 and 2. A pressurized tank 12 suitable for batch operations is filled with a fiber-forming composition 14, for example a fiber-forming composition that is suitable for making fibers useful as fabric care compositions and/or dishwashing compositions.

A pump 16 (for example a Zenith®, type PEP II pump having a capacity of 5.0 cubic centimeters per revolution (cc/rev), manufactured by Parker Hannifin Corporation, Zenith Pumps division, of Sanford, N.C., USA) is used to pump the fiber-forming composition 14 to a die 18. The fiber-forming composition's material flow to a die 18 is controlled by adjusting the number of revolutions per minute (rpm) of the pump 16. Pipes 20 are connected the tank 12, the pump 16, and the die 18 in order to transport (as represented by the arrows) the fiber-forming composition 14 from the tank 12 to the pump 16 and into the die 18. The die 18 as shown in FIG. 2 has two or more rows of circular extrusion nozzles 22 spaced from one another at a pitch P of about 1.524 millimeters (about 0.060 inches). The nozzles 22 have individual inner diameters of about 0.305 millimeters (about 0.012 inches) and individual outside diameters of about 0.813 millimeters (about 0.032 inches). Each individual nozzle 22 is encircled by an annular and divergently flared orifice 24 to supply attenuation air to each individual nozzle 22. The fiber-forming composition 14 that is extruded through the nozzles 22 is surrounded and attenuated by generally cylindrical, humidified air streams supplied through the orifices 24 encircling the nozzles 22 to produce the fibers 26. Attenuation air is provided by heating compressed air from a source by an electrical-resistance heater, for example, a heater manufactured by Chromalox, Division of Emerson Electric, of Pittsburgh, Pa., USA. An appropriate quantity of steam is added to the attenuation air to saturate or nearly saturate the heated air at the conditions in the electrically heated, thermostatically controlled delivery pipe. Condensate is removed in an electrically heated, thermostatically controlled, separator. The fibers 26 are dried by a drying air stream having a temperature of from about 149° C. (about 300° F.) to about 315° C. (about 600° F.) by an electrical resistance heater (not shown) supplied through drying nozzles (not shown) and discharged at an angle of about 90° relative to the general orientation of the fibers 26 being spun.

The fibers are collected on a collection device to form a fibrous Structure (nonwoven web) of inter-entangled fibers for example a non-random repeating pattern to a nonwoven web formed as a result of collecting the fibers on the belt or fabric.

The process for making fibrous Structures described above is more generally set forth in U.S. Provisional Application No. 61/982,469, filed Apr. 22, 2014.

Example 1: Dissolvable Porous Solid Cleanser (Fibrous Structure) with Low Hydrolysis Vinyl Acetate-Vinyl Alcohol Copolymer Table 1 below sets forth a non-limiting example of a premix (a fiber-forming composition) of the present invention for making fibers and/or a fibrous structure (nonwoven web) of the present invention via the fibrous structure making process described immediately above. The fibrous Structure is suitable for providing a beauty benefit, for example suitable for use as a shampoo.

TABLE 1

| Material | % by weight of fiber-forming composition (i.e., premix) |
|---|---|
| Low Molecular Weight, Low hydrolysis vinyl acetate-vinyl alcohol copolymer[1] | 5.13 |
| High Molecular Weight, Low hydrolysis vinyl acetate-vinyl alcohol copolymer[2] | 5.13 |
| Lauryl Hydroxysultaine (40.5% activity) | 15.4 |
| Sodium Laureth-1 Sulfate (70% activity) | 29.9 |
| Cationic cellulose (cationic polymer)[3] | 0.5 |
| Citric Acid | 0.4 |
| Distilled water | 43.54 |

[1]PVA403, Mw 30,000, 78-82% hydrolyzed, available from Kuraray America, Inc.
[2]PVA420H, Mw 75,000, 78-82% hydrolyzed, available from Kuraray America, Inc.
[3]UCARE ™ Polymer LR-400, available from Amerchol Corporation (Plaquemine, Louisiana)

Into an appropriately sized and cleaned vessel, the distilled water is added with stirring at 100-150 rpm. The cationic polymer (cationic cellulose) is then slowly added with constant stirring until homogenous. The low hydrolysis vinyl acetate-vinyl alcohol copolymer resin powders (PVA403 and PVA420H) are weighed into a suitable container and slowly added to the main mixture in small increments using a spatula while continuing to stir while avoiding the formation of visible lumps. The mixing speed is adjusted to minimize foam formation. Then the mixture is slowly heated to 75° C. for 2 hours after which the Sodium Laureth Sulfate and Lauryl Hydroxysultaine are added. The mixture is then heated to 75° C. while continuing to stir for 45 minutes and then allowed to cool to room temperature to form the premix. This premix is then ready for spinning into fibers and ultimately making the fibrous structure therefrom.

Comparative Example A—The following porous solid is not in accordance with the present invention and is included for comparative purposes only. Fibers and a fibrous structure are made from the premix described above in Table 1 except that the total level of vinyl acetate-vinyl alcohol copolymer resin powders (PVA403 and PVA420H) is replaced with the same total level of high weight average molecular weight (100,000), high hydrolysis polyvinyl alcohol copolymer resin powder (Selvol™ Polyvinyl Alcohol 523 (87-89% hydrolyzed) available from Sekisui Specialty Chemicals).

Into an appropriately sized and cleaned vessel, the distilled water is added with stirring at 100-150 rpm. The cationic polymer (cationic cellulose) is then slowly added with constant stirring until homogenous. The high weight average molecular weight, high hydrolysis polyvinyl alcohol resin powder (Selvol™ Polyvinyl Alcohol 523) is weighed into a suitable container and slowly added to the main mixture in small increments using a spatula while continuing to stir while avoiding the formation of visible lumps. The mixing speed is adjusted to minimize foam formation. Then the mixture is slowly heated to 75° C. for 2 hours after which the Sodium Laureth Sulfate and Lauryl Hydroxysultaine are added. The mixture is then heated to 75° C. while continuing to stir for 45 minutes and then allowed to cool to room temperature to form the premix. This premix is then ready for spinning into fibers and ultimately making the fibrous substrate therefrom.

Performance Comparison—For performance testing, the fibrous structure samples (Example 1 and Comparative Example A) are each cut with scissors into 1.25 gram samples on a four place balance and placed onto individual plastic weigh boats. Dimethicone with an average viscosity of 346,000 cps at 25° C. (CF330M from Momentive Performance Materials, Albany, N.Y.) is applied to each piece at a target level of 0.054 grams on a suitable four place weight balance by brushing onto the surface with a small cosmetic brush applicator. If the target weight is exceeded, the excess dimethicone is immediately removed via a small cosmetic sponge applicator. The samples are stored in bags overnight to enable the applied silicone to spread into the sample prior to testing. The dimethicone level is estimated to be approximately 4.3% by weight of the resulting sample (0.054 grams of dimethicone per 1.25 grams of sample).

The samples are tested according to the Hand Dissolution Method described herein to determine their dissolution rates. From Table 2 below, it is seen that while Example 1 of the present invention (using low hydrolysis Vinyl Acetate-Vinyl Alcohol Copolymer) exhibits excellent dissolution, Comparative Example A (using high hydrolysis polyvinyl alcohol) does not.

TABLE 2

|  | Example 1 (# of strokes) | Comparative Example A (# of strokes) |
|---|---|---|
| Dissolution Rate | 4 | >30 (gel blocking, didn't dissolve) |

B. Non-limiting Examples of Open Cell Foams

Examples 2 and 3: Dissolvable Porous Solid Cleanser (Open Cell Foam) with Low Hydrolysis Vinyl Acetate-Vinyl Alcohol Copolymer Table 3 below sets forth non-limiting examples of premixes for making an open celled foam Structure of the present invention. The premixes are formed using relatively low water (c. 60 wt %)/high solids (c. 40%) solids content. The foam Structure is suitable for providing a beauty benefit, for example suitable for use as a shampoo.

TABLE 3

| Component | Example 2 Wt % | Example 3 Wt % |
|---|---|---|
| Distilled water | qs | qs |
| Glycerin | 3.8 | 3.8 |
| Polyvinyl alcohol 420H[1] | 9.5 | 6 |
| Polyvinyl alcohol 205[2] | — | 3.5 |
| Sodium Laureth-3 sulfate | 1.8 | 1.8 |
| Sodium Laureth-1 sulfate | 12.9 | 12.9 |
| Sodium Lauryl Amphoacetate | 9.6 | 9.6 |
| Guar Hydroxypropyltrimonium Chloride[3] | 0.5 | 0.5 |
| Citric Acid | 1.8 | 1.8 |
| Total | 100 | 100 |

[1]PVA420H, Mw 75,000, 78-82% hydrolyzed, available from Kuraray America, Inc.
[2]PVA 205, Mw 39,000, 87-89% hydrolyzed, available from Sekisui Specialty Chemicals
[3]Jaguar ® C500 supplied by Solvay-Rhodia
Note that the wt % value for the Sodium Laureth-3 sulfate, Sodium Laureth-1 sulfate and Sodium Lauryl Amphoacetate in Table 3 is on final composition basis, i.e., as 100% active.

Into an appropriately sized and cleaned vessel, the distilled water is added with stirring at 100-150 rpm. The cationic polymer (cationic guar) is then slowly added with constant stirring until homogenous. The polyvinyl alcohol resins are weighed into a suitable container and slowly added to the main mixture in small increments using a spatula while continuing to stir while avoiding the formation of visible lumps. The mixing speed is adjusted to minimize foam formation. Then the mixture is slowly heated to 75° C. for 2 hours after which the Sodium Laureth Sulfates and Sodium Lauryl Amphoacetate are added. The mixture is then heated to 75° C. while continuing to stir for 45 minutes and then allowed to cool to room temperature to form the premix.

A foam is prepared from the above liquid processing mixture as described in Table 4 below via a continuous Oakes aerator and dried within an impingement oven according to the following settings and conditions:

TABLE 4

| Premix Mass Flow Rate w/FAM 10″ Die | 39.4 g/min |
|---|---|
| Oakes Air Flow Meter Setting | 56 |
| Oakes RPM | 1941 |
| Wet Density (g/cm$^3$) | 0.28 |
| Impingement Oven Temperature (° C.) | 132 |
| Drying Time (min) | 17.9 |
| Average dry substrate weight (g) | 1.1 |
| Average dry substrate density (g/cm$^3$) | 0.11 |
| Average basis weight (g/m$^2$) | 594 |

Comparative Example B—The following porous solid is not in accordance with the present invention and is included for comparative purposes only. A foam is made from the premix described above in Table 3, except no low hydrolysis (less than about 84% alcohol units) vinyl acetate-vinyl alcohol copolymer resin powders are included. Instead, only high weight average molecular weight (Mw 100,000), high hydrolysis (87-89% hydrolyzed) polyvinyl alcohol resin powder (Selvol™ Polyvinyl Alcohol 523 (87-89% hydrolyzed) available from Sekisui Specialty Chemicals) is used at 9.5 wt %.

Into an appropriately sized and cleaned vessel, the distilled water is added with stirring at 100-150 rpm. The cationic polymer (cationic guar) is then slowly added with constant stirring until homogenous. The high weight average molecular weight, high hydrolysis polyvinyl alcohol resin powder (Selvol™ Polyvinyl Alcohol 523) is weighed into a suitable container and slowly added to the main mixture in small increments using a spatula while continuing to stir while avoiding the formation of visible lumps. The mixing speed is adjusted to minimize foam formation. Then the mixture is slowly heated to 75° C. for 2 hours after which the Sodium Laureth Sulfates and Sodium Lauryl Amphoacetate are added. The mixture is then heated to 75° C. while continuing to stir for 45 minutes and then allowed to cool to room temperature to form the premix. This premix is then formed into an open cell foam according the same procedure described for Examples 2 and 3.

Performance Comparison—For performance testing, the foam samples (Examples 2 and 3 and Comparative Example B) are each cut with scissors into 1.25 gram samples on a four place balance and placed onto individual plastic weigh boats. Dimethicone with an average viscosity of 346,000 cps at 25° C. (CF330M from Momentive Performance Materials, Albany, N.Y.) is applied to each piece at a target level of 0.054 grams on a suitable four place weight balance by brushing onto the surface with a small cosmetic brush applicator. If the target weight is exceeded, the excess dimethicone is immediately removed via a small cosmetic sponge applicator. The samples are stored in bags overnight to enable the applied silicone to spread into the sample prior to testing. The dimethicone level is estimated to be approximately 4.3% by weight of the resulting sample (0.054 grams of dimethicone per 1.25 grams of sample). After application of dimethicone, a 50 gram weight is placed on the pad for 3 minutes to simulate the impact of compression and other conditions a packaged foam would encounter after being produced and placed into commerce.

The samples are tested according to the Hand Dissolution Method described herein to determine their dissolution rates. From Table 5 below, it is seen that while Examples 2 and 3 of the present invention exhibit good dissolution, Comparative Example B (using only high hydrolysis polyvinyl alcohol) does not. The data for Example 3 also demonstrate that high hydrolysis polyvinyl alcohol (e.g., PVA 205) can be used in a high % solids process to produce useful dissolvable solid Structures, so long as at least one low hydrolysis vinyl acetate-vinyl alcohol polymer is also used.

TABLE 5

|  | Example 2 (# of strokes) | Example 3 (# of strokes) | Comparative Example B (# of strokes) |
|---|---|---|---|
| Dissolution Rate | 8 | 9 | 25 |

Note that any actives and/or compositions disclosed herein can be used in and/or with the Structure, disclosed in the following U.S Patent Applications, including any publications claiming priority thereto: U.S. 61/229,981; U.S. 61/229,986; U.S. 61/229,990; U.S. 61/229,996; U.S. 61/230,000; and U.S. 61/230,004.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fibrous dissolvable solid structure comprising a plurality of fibers comprising:
    from about 3 wt % to about 75 wt % of a surfactant wherein the surfactant comprises a cationic surfactant;
    from about 10 wt % to about 50 wt % of a first copolymer comprising vinyl acetate and vinyl alcohol units, wherein the copolymer comprises not more than about 84% alcohol units and has weight average molecular weight (Mw) of from about 20,000 to about 60,000;
    from about 5 wt % to about 50 wt % of a second copolymer comprising vinyl acetate and vinyl alcohol units, wherein the second copolymer comprises not more than about 84% alcohol units alcohol units and has a Mw of from about 70,000 to about 500,000.

2. The fibrous dissolvable solid structure of claim 1, wherein the copolymer comprises not more than about 82.5% alcohol units.

3. The fibrous dissolvable solid structure of claim 2, wherein the copolymer comprises not more than about 81% alcohol units.

4. The fibrous dissolvable solid structure of claim 1, wherein the copolymer comprises from about 65% to about 82.5% alcohol units.

5. The fibrous dissolvable solid structure of claim 4, wherein the copolymer comprises from about 70% to about 81% alcohol units.

6. The fibrous dissolvable solid structure of claim 1, wherein at least 25% of the fibers have an average diameter less than about 1 micron.

7. The fibrous dissolvable solid structure of claim 6, wherein at least 50% of the fibers have an average diameter less than about 1 micron.

8. The fibrous dissolvable solid structure of claim 1, wherein the copolymer has weight average molecular weight (Mw) of from about 70,000 to about 200,000.

9. The fibrous dissolvable solid structure of claim 1, wherein the structure further comprises a perfume or fragrance.

10. The fibrous dissolvable solid structure of claim 1, wherein the structure further comprises a conditioning agent selected from the group consisting of silicone conditioning agents, cationic conditioning polymers, and combinations thereof.

11. The fibrous dissolvable solid structure of claim 1, wherein the structure comprises from about 5 wt % to about 65 wt % of the cationic surfactant.

12. The fibrous dissolvable solid structure of claim 1, wherein the structure comprises from about 23 wt % to about 75 wt % of the cationic surfactant.

13. The fibrous dissolvable solid structure of claim 1, wherein the plurality of fibers further comprise a fatty alcohol.

14. The fibrous dissolvable solid structure of claim 1, wherein the structure comprises a hand dissolution value of about 1 to about 15 strokes.

15. The fibrous dissolvable solid structure of claim 1, wherein the structure comprises a Distance to Maximum Force value of from about 6 mm to about 30 mm.

* * * * *